US009535081B2

(12) United States Patent
Yamagata et al.

(10) Patent No.: US 9,535,081 B2
(45) Date of Patent: Jan. 3, 2017

(54) AUTOMATIC ANALYSIS SYSTEM

(75) Inventors: Toshiki Yamagata, Tokyo (JP); Kenichi Takahashi, Tokyo (JP); Takahiro Sasaki, Tokyo (JP); Shigeki Yamaguchi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 426 days.

(21) Appl. No.: 14/129,598

(22) PCT Filed: Jun. 26, 2012

(86) PCT No.: PCT/JP2012/066265
§ 371 (c)(1),
(2), (4) Date: Mar. 24, 2014

(87) PCT Pub. No.: WO2013/002213
PCT Pub. Date: Jan. 3, 2013

(65) Prior Publication Data

US 2014/0314623 A1 Oct. 23, 2014

(30) Foreign Application Priority Data

Jun. 30, 2011 (JP) ................................ 2011-145165

(51) Int. Cl.

| | |
|---|---|
| ***G01N 35/02*** | (2006.01) |
| ***G01N 35/04*** | (2006.01) |
| *B01L 3/00* | (2006.01) |
| *G01N 35/00* | (2006.01) |

(52) U.S. Cl.
CPC ............ *G01N 35/02* (2013.01); *G01N 35/026* (2013.01); *G01N 35/04* (2013.01); *B01L 3/50825* (2013.01);
(Continued)

(58) Field of Classification Search
CPC ................. B01L 3/50825; G01N 2035/00287; G01N 2035/0415; G01N 2035/0405; G01N 35/02; G01N 35/026; G01N 35/04
See application file for complete search history.

(56) References Cited

U.S. PATENT DOCUMENTS

2006/0110293 A1* 5/2006 Fichera .................. G01N 35/04 422/411
2009/0056285 A1* 3/2009 Kramer .................. G01N 35/04 53/492
(Continued)

FOREIGN PATENT DOCUMENTS

JP 06230013 8/1994
JP 11281544 10/1999
(Continued)

OTHER PUBLICATIONS

International Preliminary Report on Patentability received in International Application No. PCT/JP2012/066265 dated Jan. 16, 2014.
International Search Report in PCT/JP2012/066265.

*Primary Examiner* — Jill Warden
*Assistant Examiner* — Benjamin Whatley
(74) *Attorney, Agent, or Firm* — Mattingly & Malur, PC

(57) ABSTRACT

There is provided an automatic analysis system that dispenses samples and reagents into a plurality of reaction vessels to cause reaction and to measure the liquid resulting from the reaction. The system implements a method of handling capped sample containers such as vacuum blood collection tubes along transfer routes. A sample container opening/closing mechanism is provided which removes the caps of the sample containers prior to sample dispensing and which closes the sample containers following sample dispensing using the same corresponding caps as before the dispensing. Also provided is an opening/closing mechanism that retains and manages the caps removed from the sample containers, as well as a transport unit capable of selecting one of the transport routes which fits the identified sample containers so as to close them with the fit caps. This invention thus provides a container opening/closing system that improves throughput of the sample collection process in conjunction with the automatic analysis system performing the sample container opening/closing process.

9 Claims, 63 Drawing Sheets

(52) U.S. Cl.
CPC ............... *G01N 2035/00287* (2013.01); *G01N 2035/0415* (2013.01)

(56) References Cited

U.S. PATENT DOCUMENTS

| | | | | |
|---|---|---|---|---|
| 2011/0003377 | A1* | 1/2011 | Itoh | G01N 35/00 435/307.1 |
| 2011/0088517 | A1* | 4/2011 | Tsujimura | G01N 35/026 81/3.09 |
| 2012/0321516 | A1* | 12/2012 | Schacher | G01N 35/04 422/68.1 |

FOREIGN PATENT DOCUMENTS

| | | | |
|---|---|---|---|
| JP | 2000105246 | | 11/2000 |
| JP | 2003315348 | | 11/2003 |
| JP | 2004085521 | | 3/2004 |
| JP | 2008168938 | | 7/2008 |
| JP | 2009036511 | A * | 2/2009 |
| JP | 2009141957 | | 6/2009 |
| JP | 2009264878 | | 11/2009 |
| JP | 2012159317 | | 8/2012 |
| WO | 2013002216 | | 1/2013 |

* cited by examiner

<PROCESS 1-5>
SAMPLE DISPENSING
PROCESS

<PROCESS 1-6>
RACK TRANSPORTED

<PROCESS 1-7>
CAP CLOSING
PROCESS (1)

<PROCESS 1-8>
CAP CLOSING
PROCESS (2)

<PROCESS 1-1>
RACK CARRIED IN

<PROCESS 1-2>
CAP OPENING
PROCESS (1)

<PROCESS 1-3>
CAP OPENING
PROCESS (2)

<PROCESS 1-5>
SAMPLE DISPENSING
PROCESS

<PROCESS 1-7>
CAP CLOSING
PROCESS (1)

<PROCESS 2-1>
RACK CARRIED IN

<PROCESS 1-8>
CAP CLOSING
PROCESS (2)

<PROCESS 2-2>
CAP OPENING
PROCESS (1)

<PROCESS 1-9>
RACK CARRIED OUT

<PROCESS 2-3>
CAP OPENING
PROCESS (2)

<PROCESS 2-5>
SAMPLE DISPENSING PROCESS

<PROCESS 2-6>
RACK TRANSPORTED

<PROCESS 2-8>
CAP CLOSING
PROCESS (2)

<PROCESS 3-2>
CAP OPENING
PROCESS (1)

<PROCESS 2-9>
RACK CARRIED OUT

<PROCESS 3-3>
CAP OPENING
PROCESS (2)

<PROCESS 3-4>
RACK TRANSPORTED

<PROCESS 3-5>
SAMPLE DISPENSING
PROCESS

<PROCESS 3-6>
RACK TRANSPORTED

<PROCESS 3-7>
CAP CLOSING PROCESS (1)

<PROCESS 4-1>
RACK TRANSPORTED

<PROCESS 3-8>
CAP CLOSING
PROCESS (2)

<PROCESS 4-2>
CAP OPENING
PROCESS (1)

AUTOMATIC ANALYSIS SYSTEM

TECHNICAL FIELD

The present invention relates to an automatic analysis system for analyzing biological samples such as blood and urine. More particularly, the invention relates to an automatic analysis system equipped with an opening/closing unit for opening and closing containers holding the samples.

BACKGROUND ART

The automatic analysis system is a system that includes an automatic analysis unit for measuring the physical properties of samples given as the measuring object (e.g., biological samples such as blood serum and urine, or liquid mixtures of samples with reagents) for analysis purposes. Also included are processing units that perform diverse processes such as a container cap opening process, a dispensing process, a container cap closing process, a stirring process, and an analyzing process.

In connection with the container cap opening and closing processes of the above-mentioned automatic analysis system, there exist prior-art techniques of an opening/closing unit that opens and closes the caps of sample containers (called the cap opening process and the cap closing process hereunder), such as the opening/closing means described in Patent Literatures 1 through 4 cited below. With regard to a container transporting process of the automatic analysis system, there exist prior-art techniques for container transportation such as the transport means described in Patent Literature 5 cited below.

A cap opening unit described in Patent Literature 1 offers a cap opening method for opening a plurality of caps at the same time. An opening/closing unit described in Patent Literature 2 offers an opening/closing method whereby the opening/closing unit moves rotatively while holding container caps and performs the dispensing process and cap closing process in the same position as in the cap opening process. An opening/closing unit described in Patent Literature 3 offers a method whereby, after performing the container cap opening process, the opening/closing unit moves on while holding the container caps and carries out the dispensing process and cap closing process in the same position as in the cap opening process. An opening/closing unit described in Patent Literature 4 offers a method whereby, after performing the process of opening the cap of a container, the opening/closing unit holds the cap and allows the container to move rotatively to perform the dispensing process in a position different from the position where the cap opening process was performed, and carries out the cap closing process in the same position as in the cap opening process. The transfer means described in Patent Literature 5 offers a rack buffer mechanism furnished with a plurality of holding positions.

PRIOR ART LITERATURE

Patent Literature

Patent Literature 1: JP-4210306-B
Patent Literature 2: JP-3273916-B
Patent Literature 3: JP-6-230013-A
Patent Literature 4: JP-2009-264878-A
Patent Literature 5: JP-3668618-B

SUMMARY OF THE PRESENT INVENTION

Problem to be Solved by the Invention

Whereas the opening/closing unit described in Patent Literature 1 offers the cap opening method whereby a plurality of container caps are opened at the same time, the method involves having a pair of clamping members moved upward while lifting the clamping members so as to remove the caps from test tubes. This poses the problem of having to limit the types of caps that may be used.

The opening/closing units described in Patent Literatures 2 and 3 offer the opening/closing methods whereby the opening/closing unit moves while holding caps following the container cap opening process and performs the dispensing process and cap closing process in the same position as in the cap opening process. However, the fact that the dispensing position, cap opening position, and cap closing position are the same poses the problem of having throughput determined by the time it takes to go through a cycle ranging from opening to closing of caps. If it takes, say, 10 seconds to go from opening to closing of the caps, the maximum throughput is about 360 tests/hour.

The opening/closing unit described in Patent Literature 4 offers the method whereby, after performing the container cap opening process, the opening/closing unit holds the cap and allows the container to move rotatively to perform the dispensing process in a position different from the position where the cap opening process was performed, and carries out the cap closing process in the same position as in the cap opening process. In this case, there is only one container transport path, which poses the problem of making the simultaneous processing of a plurality of containers difficult to achieve.

The opening/closing unit described in Patent Literature 5 offers a rack buffer mechanism equipped with a plurality of holding positions. Given transport means for successively transporting one container after another along a linear transport path, the unit makes it possible quickly to process the sample containers to be analyzed preferentially. However, this Patent Literature has no mention of performing a cap opening/closing process. An operator is required manually to open and close the caps of sample containers. That means it takes time to perform processes before and after the analysis.

An object of the present invention is to provide an automatic analysis system equipped with a cap opening/closing mechanism for solving the above problem and improving throughput.

Means for Solving the Problem

In view of solving the above problem, the present invention may be embodied as follows:

There is provided an automatic analysis system including a transport unit for transporting sample containers which have removable caps and which contain samples, a sample processing unit which processes the samples contained in the sample containers, and a cap opening/closing unit which opens and closes the caps of the sample containers.

The transport unit includes a first transport line which transports the sample containers to the sample processing unit, a second transport line which transports the sample containers having undergone processing of the samples by the sample processing unit, and a third transport line which transports the sample containers from the first or the second transport line to the cap opening/closing unit and which returns to the first or the second transport line the sample containers having undergone a cap opening process or a cap closing process.

Effect of the Present Invention

According to the present invention, there may be provided an automatic analysis system furnished with a cap opening/closing mechanism for enhancing throughput.

MODE FOR CARRYING OUT THE INVENTION

The first embodiment of the present invention is explained below with reference to the accompanying drawings. It should be noted that this embodiment is presented only as an example and is not limitative of the present invention.

Figure 1:
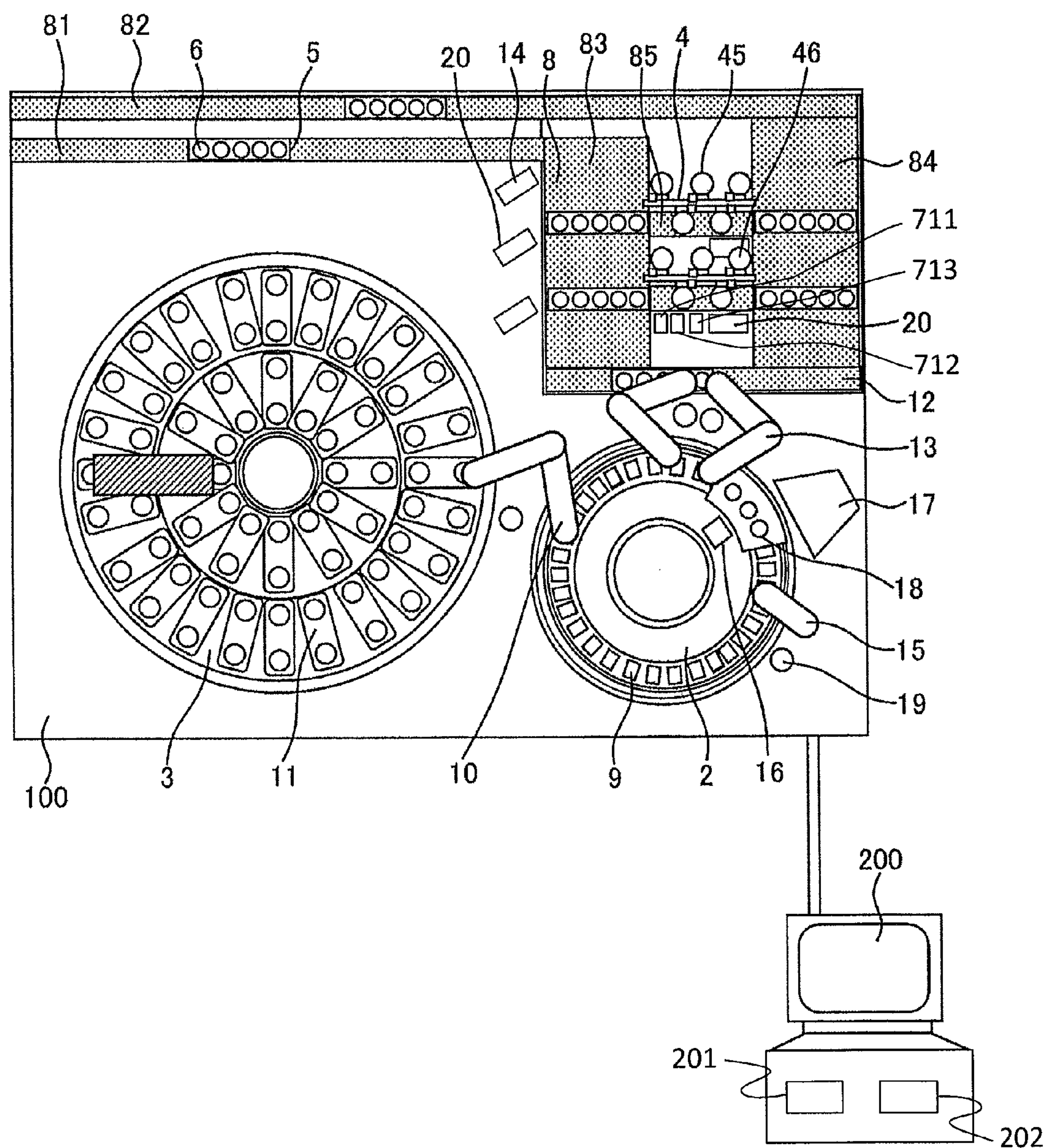
FIG. 1 is a schematic view showing an overall configuration of an automatic analysis system as a first embodiment of the present invention.

FIG. 1 is a schematic plan view showing an overall configuration of an automatic analysis system as the first embodiment of the present invention. As shown in FIG. 1, the automatic analysis system 100 is furnished with a transport unit 8 which carries sample containers 6 which has caps 7 and containing samples such as blood, urine, or other biological samples, the sample containers being mounted on a rack 5 for transport purposes; and an opening/closing unit 4 that performs the processes of opening and closing the caps of the sample containers 6 transported by the transport unit 8. Although the transport unit 8 has just been explained as capable of transporting the sample containers 6 mounted on the rack 5, the unit may alternatively be structured to transport solely the sample containers 6 without mounting them on the rack 5. As another alternative, whereas the rack 5 shown in FIG. 5 is of a type that carries a plurality of sample containers, the rack 5 may be of another type that transports one sample container at a time.

As shown in FIG. 1, there is provided a unidirectionally rotatable reaction disk 2 mounted on a housing 1. The reaction disk 2 is structured to let a plurality of reaction vessels 9 be positioned regularly along the circumference of the disk. Adjacent to the reaction disk 2 is a reagent disk 3. The reagent disk 3 is structured to be bidirectionally rotatable, rotating in a direction where the necessary reagent is positioned close to a reagent probe 10. Mounted along the entire circumference of the reagent disk 3 are reagent vessels 11 containing diverse reagents each for use in analyses. The reagent probe 10 is connected to a reagent pump, not shown. The reagent probe 10 is structured to pick up a predetermined amount of reagent from reagent vessels 11 on the reagent disk 3 and dispense the reagent into reaction vessels 9 on the reaction disk 2.

The transport unit 8 is made up of a supply line 81, a first transport line 83, a sample line 12, a second transport line 84, a third transport line 85, and a return line 82.

Although the transport unit 8 has just been explained as composed of the supply line 81, first transport line 83, sample line 12, second transport line 84, third transport line 85, and return line 82 for convenience of explanation, the supply line 81 and the return line 82 may not be provided. Also, the first transport line 84 may be structured to include the supply line 82, and the second transport line 85 may be structured to include the return line 82. Further, although the sample line 12 was explained as being set up independently for convenience of explanation, the sample line 12 may alternatively be structured to be included in the first transport line 83 and the second transport line 84.

The supply line 81 is connected to a carry-in entrance, not shown, which is located at one edge of the housing 1 and through which the sample containers 6 are carried in from outside the automatic analysis system 100. The supply line 81 is extended from one edge of the housing 1 to just short of the reaction disk 2. The other end of the supply line 81 is connected to one end of the first transport line 83. The supply line 81 is structured to let the rack 5 advance in its longitudinal direction. The first transport line 83 is structured to extend in a short direction of the rack 5 over the supply line 81.

The sample line 12 is a line that transports the rack 5 close to the reaction disk 2. Sample probes 13 that can rotate and move up and down are provided between the reaction vessels 9 and the sample line 12. The sample probes 13 may not only be arranged to rotate and move up and down but also be attached to an XYZ transport mechanism, each of the probes being connected to a sample pump, not shown.

A cap opening/closing unit 4 is installed around the sample line 12. With this embodiment, the opening/closing unit 4 is located between the first transport line 83 and the second transport line 84 and over the third transport line 85 to and from which sample containers can be carried in and out bidirectionally from any of the two lines. Since the opening/closing unit 4 is not located over any of the first transport line 83 and second transport line 84, the rack will not be stranded on the transport unit because of the opening and closing process being underway. Because the opening/closing unit 4 can be accessed from both the first transport line 83 and the second transport line 84, the caps removed in a cap opening process can be easily attached again to the sample containers in a cap closing process.

A stirring unit 15, a light source 16, an optical detector 17, and a vessel cleaning mechanism 18 are provided around the reaction disk 2. The vessel cleaning mechanism 18 is connected to a cleaning pump, not shown. A cleaning port 19 is installed within the operating range of each of the sample probes 13, reagent probe 10, and stirring unit 15. A control computer 200 acting as a control unit is connected electrically with the sample pump (not shown), reagent pump (not shown), cleaning pump (not shown), optical detector 17, reaction vessels 9, reagent disk 3, reagent probe 10, and sample probes 13.

Near the opening/closing unit 4, there are provided a sample information identification unit 14 sealed in a sample container 6 and an ID reading unit 20.

The sample information identification unit 14 may be an imaging device such as a CCD that analyzes images of the sample containers 6 to identify each sample container 6 (in diameter, height, and type), determine whether the cap of the sample container 6 in question is opened (presence or absence of a cap 7), and identify the type of each cap 7. Alternatively, the sample information identification unit 14 may detect the presence or absence of the caps 7 and identify the type of each cap 7 using a detection method other than image recognition. For example, a light-emitting device and a light-receiving device may be positioned facing each other so that the output of the light-receiving device may be detected to recognize the presence or absence of the caps 7 and recognize the type of each cap 7. As another alternative, the presence or absence of the caps 7 may be detected using some other suitable method.

Further, the ID reading unit 20 is a unit that identifies sample information about the sample contained in each sample container. As such, the ID reading unit 20 may be a barcode reader, an RFID reading antenna, an imaging device or the like. The sample information may include the date of acceptance of a given sample, the acceptance number of the sample, attribute of the patient involved, etc. The sample information may be stored on a storage medium such as a barcode pasted on each sample container or in an information medium such as an RFID tag attached to a carrier transporting each sample container.

Alternatively, the content of processing of each sample may be determined based on information coming from a host control computer, without recourse to the sample information identification unit 14 or ID reading unit 20.

The transport unit 8, opening/closing unit 4, sample information identification unit 14, and ID reading unit 20 are connected electrically to the control computer 200 acting as a control unit.

Figure 2A:
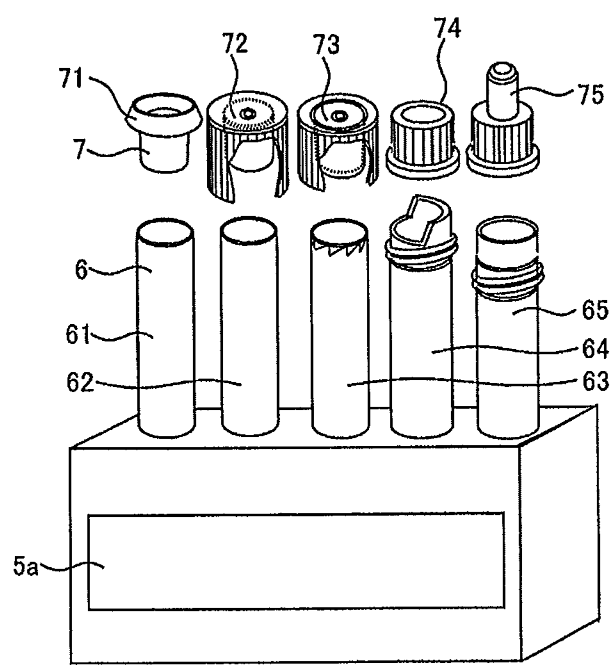
FIG. 2A is an illustration showing a plurality of sample containers according to the first embodiment of the present invention.
Figure 2B:
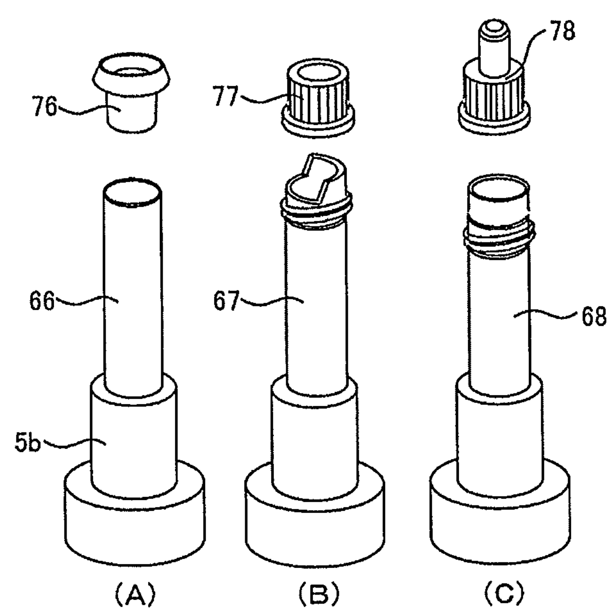
FIG. 2B is the illustration showing a plurality of sample containers according to the first embodiment of the present invention.

FIGS. 2A and 2B are perspective views of sample containers 6 provided with a plurality of types of caps 7. Each sample container 6 has an opening through which a sample is introduced or taken out. The opening is closed by a cap 7 that prevents the entry of foreign matter, evaporation or condensation of what is contained, or spilling of the sample from a falling container. These sample containers 6 are each closed with a cap 7 before being mounted on a rack 5*a* or a holder 5*b* and input to the automatic analysis system by an operator. The carrier transporting the sample containers may be a rack type carrier that can transport a plurality of sample containers at one time as shown in FIG. 2A, or a holder type carrier that transports one sample container at a time as depicted in subfigures (A), (B) and (C) of FIG. 2B.

Figure 3A:
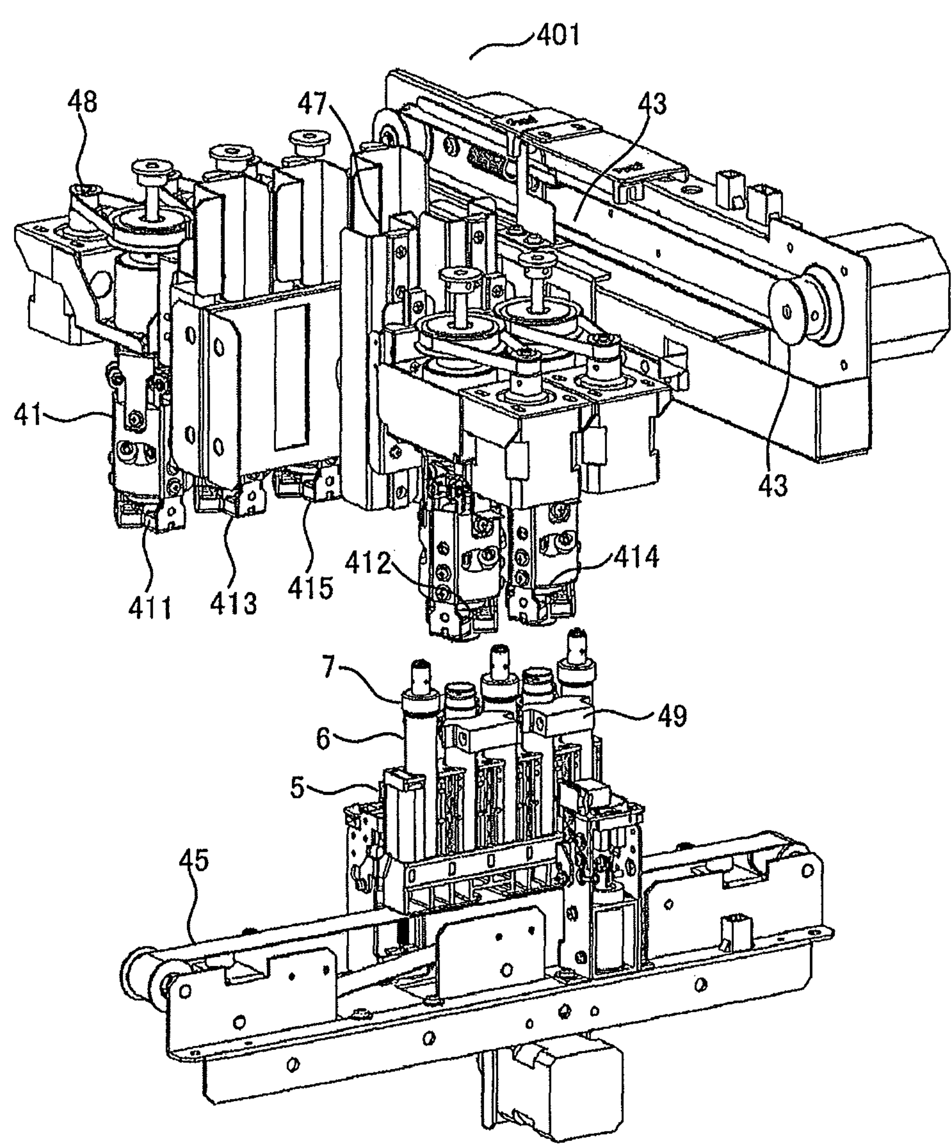
FIG. 3A is a schematic view showing a structure of an opening/closing unit of the present invention.

FIG. 3A is a schematic view of an opening/closing unit 401. The major components of the opening/closing unit 401 are a transport arm 43, a chuck up/down mechanism 47, a chuck rotation mechanism 48, a clamp mechanism 49 for clamping sample containers 6, and a chuck mechanism 41.

The transport arm 43 moves the chuck mechanisms 41 (411-415). Shown in the drawing is a method whereby a cap chuck mechanism is moved in the directions of the X and Z axes that are provided. However, present invention is not limitative of this method. Alternatively, the chuck mechanism may be rotatively moved around an axis, for example.

The clamp mechanism 49 clamps and lifts the sample containers 6, the actions being needed upon opening and closing of their caps.

The chuck mechanism 41 performs the processes of opening and closing the caps 7. The chuck mechanism 41 causes the up/down mechanism 47 and rotation mechanism 48 to perform the cap opening process and cap closing process. The chuck mechanism 41 also has the function of retaining the removed caps 7 until they are used in the cap closing process. Meanwhile, there may be provided a disposal area 701 for caps 7 close to the opening/closing unit 401 so that if the removed caps 7 are no longer needed, they may be placed in this area for disposal. Also a supply area 702 of caps 7 may be provided near the opening/closing unit 401. This area may be used to supply the caps 7 that are exclusively used to close the sample containers.

Also, the sample information identification unit 14 may be installed near the opening/closing unit 401. Given a sample container 6 whose cap cannot be removed or attached successfully, this structure will allow a retry operation to be performed on the container in question as many times as predetermined.

Further, there may be provided a temperature control mechanism 711, a humidifying mechanism 712, and a cleaning mechanism 713, all not shown, near the opening/closing unit. Each removed cap 7 may then be subjected to temperature and humidity control of the mechanisms to prevent drying of the sample attached to the cap 7. In addition, the cap cleaning mechanism 713 (not shown) may be used to clean the sample from each removed cap 7.

First Embodiment

Explained next is an analytical procedure using the automatic analysis system as the first embodiment of the present invention. In conjunction with the first embodiment, there will be explained a case where one transfer line A 45 serving as the third transport line is provided for one opening/closing unit.

Prior to analysis, the automatic analysis system is subjected to maintenance. Maintenance work typically involves inspecting the optical detector 17, cleaning the reaction vessels 9, and cleaning various probes such as the sample probes 13. Thereafter, samples serving as the test object such as blood or urine are sealed into the sample containers 6 which, still capped with the caps, are placed onto the rack 5 and transferred by the transport unit 8.

The sample information identification unit 14 installed around the transport unit 8 reads sample information to identify each sample container 6 (in diameter, height, and type). The sample information identification unit 14 also determines the presence or absence of the cap 7 of each sample container 6 and identifies the type of each cap 7 (rubber cap, plastic guard cap, screw cap, etc.) at the same time. The sample information identification unit 14 images the sample containers 6 to acquire their images and analyzes the acquired images to determine the opened/closed state of the sample containers 6 (i.e., presence or absence of their caps 7) and identify the type of each cap 7. In this manner, the types and attributes of the sample containers 6 and their caps 7 are stored into a storage unit 201 inside the control computer 200 as the information about the sample containers 6 together with the date of acceptance of each sample, the acceptance number of the sample, attribute of the patient involved, etc. Based on the stored information, a sample information management unit 202 inside the control computer 200 determines whether the processes of opening and closing each sample container 6 are possible, and performs other processes as well.

The sample information management unit 202 in the control computer 200 determines the processing details of each sample (whether its container is opened or not, and the destination of the rack 5) based on the analyzed information. In this respect, the processing details of each sample may be determined alternatively based on information coming from the host control computer 200. On the basis of the identification process that involved reading of the information as described above, the destination of the rack 5 is determined (i.e., the position where the caps are opened by the opening/closing unit 401 or by the opening/closing unit 402).

Incidentally, the sample information management unit 202 stores beforehand the information necessary for the opening and closing of caps (torque, operating conditions, and conditions for determining anomaly) in a manner fit for the type of the sample containers 6 (e.g., blood collection tube). If a plurality of opening/closing units are provided, the information about the use status of these units may also be stored in advance. The use status of the opening/closing units includes information as to whether the cap opening process and cap closing process are carried out or not and whether the removed caps are being retained or not.

Next, the ID reading unit 20 performs the process of identifying the rack 5 and sample containers 6. The ID reading unit 20 reads sample identifying information such as sample IDs from RFID tags or sample barcodes pasted on the rack 5 and sample containers 6. The sample identifying information thus read is transmitted to the sample information management unit 202 inside the control computer 200 and registered therein along with the information about the opening/closing unit 4 performing the cap opening process, about the identity of the sample containers 6 (in diameter, height, and type), about the presence or absence of the caps 7, and about the cap types (rubber cap, plastic guard cap, screw cap, etc.).

The rack 5 on which the sample containers 6 were identified by the ID reading unit 20 is transferred to the cap opening/closing units (401, 402). Given the identification of the sample containers 6 read by the sample information identification unit 14, optimal operating conditions for the opening/closing unit 4 are determined in accordance with the conditions registered in the sample information management unit 202. Based on the operating conditions thus determined, the opening/closing units (401, 402) perform the cap opening process. In keeping with the information from RFID tags on which the sample information is registered or with the information from sample barcodes, the cap opening/closing unit 4 recognizes the type of each cap 7 and opens it accordingly. The caps 7 thus opened are retained by the cap opening/closing unit 4. The processes of opening and closing the caps 7 will be described later in detail.

The sample containers 6 with their caps 7 removed are transferred to the sample line 12 by the transport unit 8. The sample containers 6 transferred onto the sample line 12 are transported to a sample collection position where the sample probes 13 perform a sample dispensing process. The samples collected by the sample probes 13 are dispensed by a predetermined amount into the reaction vessels 9 arranged on the reaction disk 2. A predetermined amount of reagent is dispensed into the reaction vessels 9 after being taken from the reagent vessels 11 by the reagent probe 10. The stirring unit 15 stirs the reaction vessels 9 for a predetermined time period for reaction purposes, before the optical detector 17 measures the samples in the reaction vessels 9 for absorbance, spectrum, etc. The results of the measurement are output to the control computer 200. Where further items of measurement are requested, the sample dispensing operations described above are repeated for each of the items. The sample dispensing process is repeated likewise until it is complete when all predetermined measurement items for the samples in all sample containers 6 on the rack 5 have been dealt with.

The rack 5 on which the sample dispensing process is completed is transferred back to the opening/closing position of the opening/closing unit 4 that has performed the cap opening process. The ID reading unit 20 reads the information of the rack 5 carrying the dispensed sample containers 6 so as to determine the cap opening/closing unit that should perform the cap closing process.

Since the opening/closing unit that has carried out the cap closing process retains and manages the caps 7 removed from the sample containers 6, the sample containers 6 transferred to the opening/closing position of the same opening/closing unit that has removed the caps 7 are then capped thereby with the same caps removed before the dispensing process. The sample containers 6 with their caps 7 attached again are transferred by the transport unit 8 to a sample holding unit, not shown.

Figure 3B:
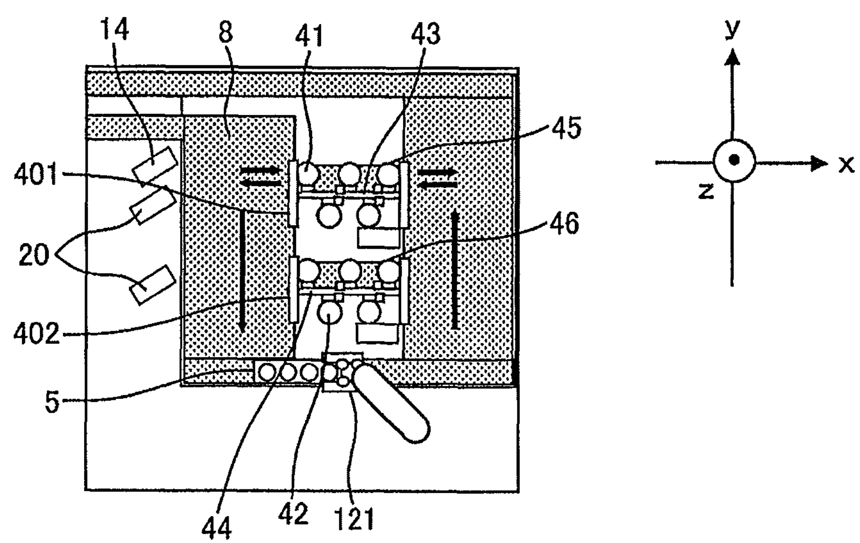
FIG. 3B is a schematic view showing a structure of the opening/closing unit according to the first embodiment of the present invention.
Figure 3C:
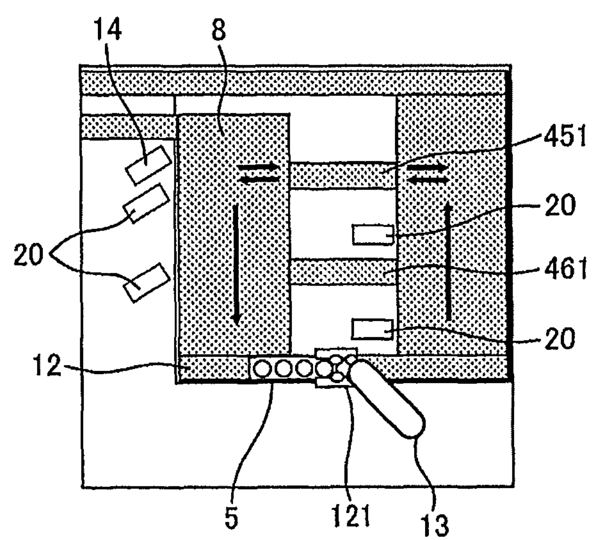
FIG. 3C is a schematic view showing a structure of a transport unit according to the first embodiment of the present invention.

FIGS. 3B and 3C are schematic plan views showing the first opening/closing unit 401 and second opening/closing unit 402 furnished with a transfer line A 45 and a transfer line B 46, respectively, as the third transport line for each opening/closing unit.

In the opening/closing position on the rack 5 transferred by the transport unit 8, the sample information identification unit 14 determines cap status. If the control computer determines that the cap opening process is necessary, the control computer notifies the transport unit of the necessity, references the sample information management unit 202 to determine the opening/closing unit that can perform the cap opening process on the rack in question, and informs the transport unit of the opening/closing unit thus determined.

The transport unit transports the rack along the first transport line. As the rack arrives at a branching point between the first transport line 83 and the third transport line 85 having the opening/closing unit 401 or 402 designated to perform the cap opening process, the ID reading unit 20 installed nearby reads the identification information on the sample containers or on the rack. The identification information thus read is transmitted to the sample information management unit 202 of the control computer and stored therein along with the information identifying the opening/closing unit that performs the cap opening process.

The cap opening/closing units (401, 402) are principally equipped with chuck mechanisms (41, 42) that perform the cap opening and closing processes and retain the removed caps for management purposes, the transport arms (43, 44) that transport the chuck mechanisms, and the transfer lines A 45 and B 46 capable of transferring the rack 5 in reciprocating motion. The transport arms (43, 44) are principally furnished with drive mechanisms capable of moving the chuck mechanisms (41, 42) in three axial directions (Y, Y, and Z directions). The chuck mechanisms (41, 42) are capable of performing the processes of opening and closing the caps 7 and retaining the removed caps 7 until the cap closing process is carried out. Alternatively, the transport arms may be structured to move the chuck mechanisms in two axial directions so as to move test tubes in these directions accordingly.

FIG. 3C is a schematic view in which the chuck mechanisms (41, 42) of the cap opening/closing units (401, 402) and the transport arms (43, 44) are not shown. The transfer line A 45 composed of a transfer line 451 is provided as a transfer line subject to the opening and closing processes by the first opening/closing unit 401, and the transfer line B 46 made of a transfer line 461 is provided as a transfer line subject to the opening and closing process by the second opening/closing unit 402.

The opening/closing units (401, 402) of this embodiment are capable of simultaneously opening and closing a plurality of sample containers 6 mounted on the rack 5.

FIGS. 7A through 7F show the operating procedure of the cap opening process and cap closing process performed when there is one transfer line A 45 (opening/closing position) for the rack 5 according to the first embodiment.

(Cap Opening Process 1)

Figure 7A:
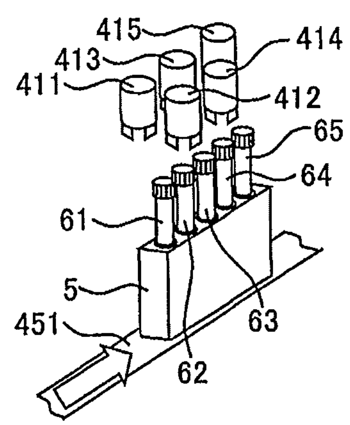
FIG. 7A is a diagram of a movement pattern involving the process of opening the caps of sample container according to the first embodiment of the present invention.

The rack 5 transported from the supply line 81 to the first transport line 83 is transported from there to the cap opening position on the transfer line 451 as the third transport line for the cap opening process. The transport arm 43, not shown, moves in the three axial directions to transport the cap chuck mechanisms (411-415) to a position fit for the process of opening the caps of the sample containers 61 through 65 mounted on the rack 5. The transport arm waits after the cap opening position is reached (FIG. 7A).

(Cap Opening Process 2)

Figure 7B:
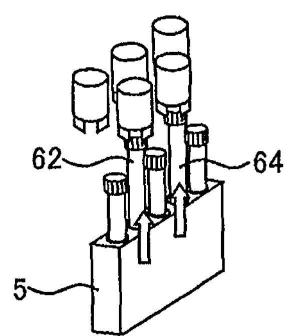
FIG. 7B is the diagram of the movement pattern involving the process of opening the caps of sample container according to the first embodiment of the present invention.

Of the five sample containers mounted on the rack 5, the sample containers 62 and 64 are first subjected to the cap opening process. The sample containers 62 and 64 are lifted to a predetermined height by a sample container clamping mechanism, not shown (FIG. 7B).

(Cap Opening Process 3)

Figure 7C:
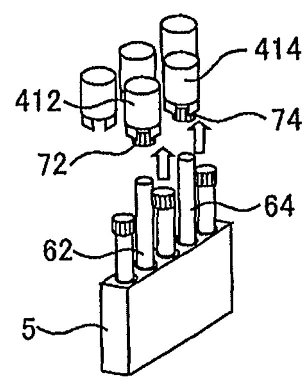
FIG. 7C is the diagram of the movement pattern involving the process of opening the caps of sample container according to the first embodiment of the present invention.

The chuck mechanisms (412, 414) clutch the caps of the sample containers (62, 64) and perform a suitable cap opening process according to the cap type. The caps (72, 74) removed from the sample containers (62, 64) are retained by the chuck mechanisms (412, 414) that have performed the cap opening process (FIG. 7C).

(Cap Opening Process 4)

Figure 7D:
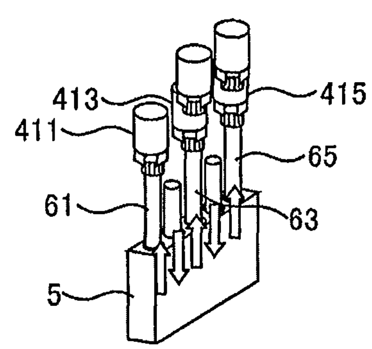
FIG. 7D is the diagram of the movement pattern involving the process of opening the caps of sample container according to the first embodiment of the present invention.

Next, the remaining sample containers (61, 63, 65) on the rack 5 are lifted to the predetermined height by the sample container clamping mechanism, not shown (FIG. 7D).

(Cap Opening Process 5)

Figure 7E:
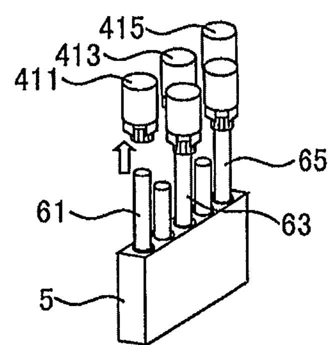
FIG. 7E is the diagram of the movement pattern involving the process of opening the caps of sample container according to the first embodiment of the present invention.

The chuck mechanisms (411, 413, 415) clutch the caps of the sample containers (61, 63, 65) and perform a suitable cap opening process according to the cap type. The caps (71, 73, 75) removed from the sample containers (61, 63, 65) are retained by the chuck mechanisms (411, 413, 415) that have performed the cap opening process (FIG. 7E).

(Cap Opening Process 6)

Figure 7F:
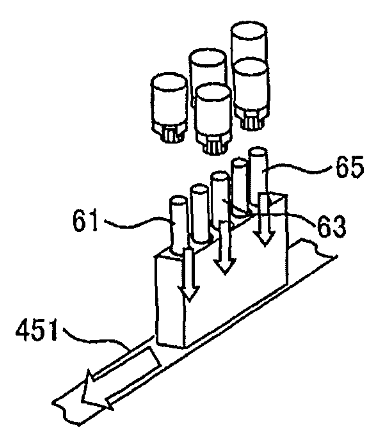
FIG. 7F is the diagram of the movement pattern involving the process of opening the caps of sample container according to the first embodiment of the present invention.

The sample containers (61, 63, 65) on which the cap opening process has ended are lowered to the installation position of the rack 5 by the sample container clamping mechanism, not shown. When the cap opening process has ended on all sample containers 5 it carries, the rack 5 is transported from the transfer line 451 back to the first transport line 83 (FIG. 7F).

The operations of the cap closing process are outlined in FIGS. 7G through 7L.

(Cap Closing Process 1)

Figure 7G:
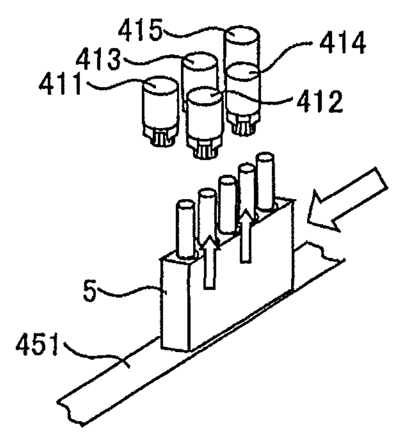
FIG. 7G is a diagram of a movement pattern involving the process of closing the caps of sample container according to the first embodiment of the present invention.

The rack 5 on which the dispensing process has ended is transported from the second transport line 84 to the cap closing position on the transfer line 451. The transport arm 43, not shown, moves in the three axial directions to transport the chuck mechanisms 411 through 415 to a position fit for the sample containers on the rack 5 to be capped with their caps. The transport arm waits after the cap closing position is reached (FIG. 7G).

(Cap Closing Process 2)

Figure 7H:
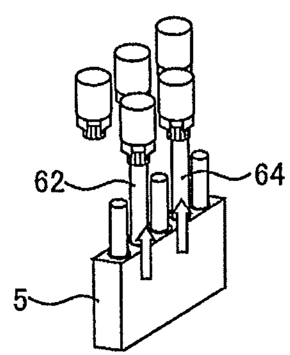
FIG. 7H is the diagram of the movement pattern involving the process of closing the caps of sample container according to the first embodiment of the present invention.

Of the five sample containers mounted on the rack 5, the sample containers 62 and 64 are first subjected to the cap closing process. The sample containers 62 and 64 are lifted to the predetermined height by the sample container clamping mechanism, not shown (FIG. 7H).

(Cap Closing Process 3)

Figure 7I:
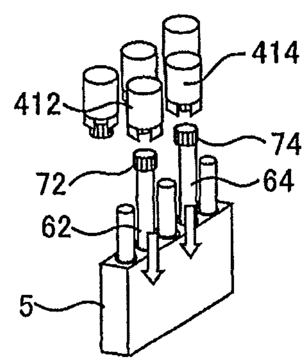
FIG. 7I is the diagram of the movement pattern involving the process of closing the caps of sample container according to the first embodiment of the present invention.

The chuck mechanisms (412, 414) holding caps perform a suitable cap closing process on the sample containers (62, 64) according to the cap type. This allows the sample containers (62, 64) to be capped with their original caps (72, 74) removed by the chuck mechanisms (412, 414) before the dispensing process (FIG. 7I).

(Cap Closing Process 4)

Figure 7J:
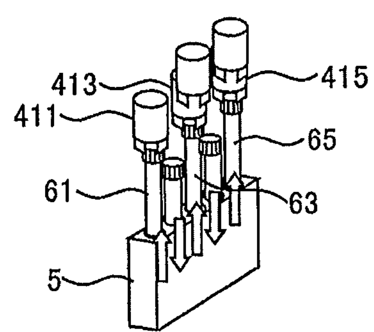
FIG. 7J is the diagram of the movement pattern involving the process of closing the caps of sample container according to the first embodiment of the present invention.

Next, the remaining sample containers (61, 63, 65) on the rack 5 are lifted to the predetermined height by the sample containing clamping mechanism, not shown (FIG. 7J).

(Cap Closing Process 5)

Figure 7K:
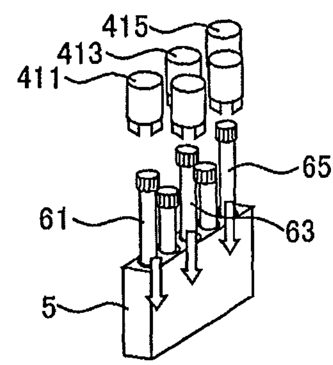
FIG. 7K is the diagram of the movement pattern involving the process of closing the caps of sample container according to the first embodiment of the present invention.

The chuck mechanisms (411, 413, 415) holding caps perform a suitable cap closing process on the sample containers (61, 63, 65) according to the type of the caps being held. This allows the sample containers (61, 63, 65) to be capped with their original caps (71, 73, 75) removed by the chuck mechanisms (411, 413, 415) before the dispensing process (FIG. 7K).

(Cap Closing Process 6)

Figure 7L:
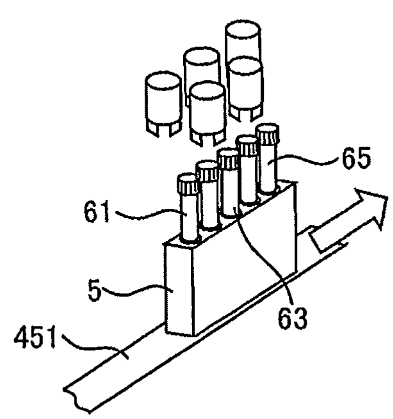
FIG. 7L is the diagram of the movement pattern involving the process of closing the caps of sample container according to the first embodiment of the present invention.

The sample containers (61, 63, 65) on which the cap closing process has ended are lowered to the installation position of the rack 5 by the sample container clamping mechanism, not shown. Thereafter, the rack 5 is discharged from the transfer line 451 (FIG. 7L).

FIGS. 4A through 4J show the movement patterns of the rack ranging from the cap opening process to the cap closing process involving the use of the cap opening/closing unit 4 structured as described above.

(Process 1-1)

Figure 4A:
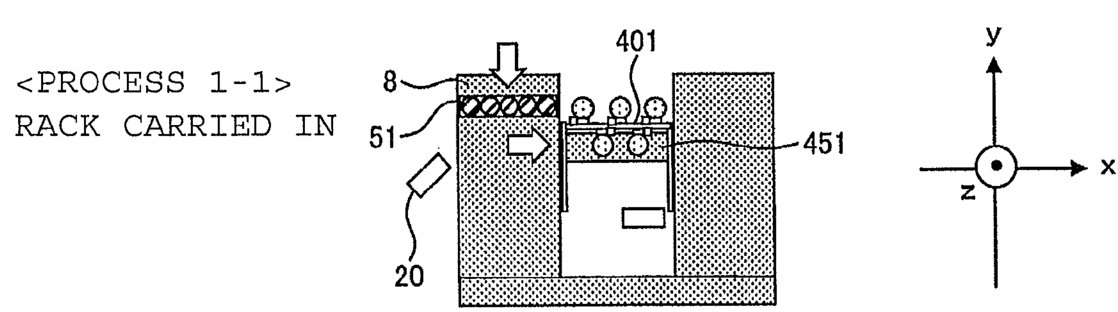
FIG. 4A is a diagram of a movement pattern ranging from the carrying-in of a first sample container to the process of opening the cap thereof according to the first embodiment of the present invention.

The rack 51 transported from the supply line 81 to the first transport line 83 is transferred by a slide mechanism of the transport unit 8 to the transfer line 451 on which the opening/closing process can be performed by the opening/closing unit 4. The transfer line 451 (i.e., cap opening/closing position) is determined by the ID reading unit 20 and control computer 200 (FIG. 4A). In this determination process, the ID reading unit 20 identifies the sample information and queries the sample information management unit 202 of the control computer 200. The control computer 200 determines whether or not to transfer the sample containers in question to the opening/closing unit 4 by referencing the status of the unit 4 (whether the opening/closing unit 4 is performing the cap opening or closing process on other sample containers, whether the unit 4 is holding the caps of other sample containers, etc.). Based on the result of the determination, the transport unit 8 transports the sample containers to the transfer line 451 or causes them to wait on the first transport line 83.

Incidentally, five sample containers are mounted on the rack 51 with this embodiment. At the time of the process 1-1, all containers are shown capped with their caps.

(Process 1-2)

Figure 4B:
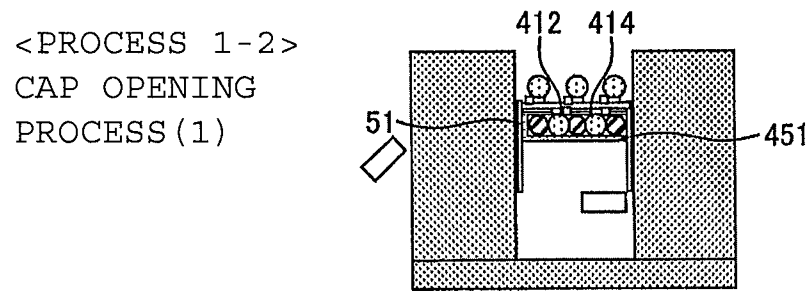
FIG. 4B is the diagram of the movement pattern ranging from the carrying-in of the first sample container to the process of opening the cap thereof according to the first embodiment of the present invention.

When the sample containers are transported to the transfer line 451, the chuck mechanisms (412, 414) of the opening/closing unit 4 open the caps (72, 74) of the sample containers (62, 64) on the rack 51. The removed caps (72, 74) are held by the chuck mechanisms (412, 414) (FIG. 4B).

(Process 1-3)

Figure 4C:
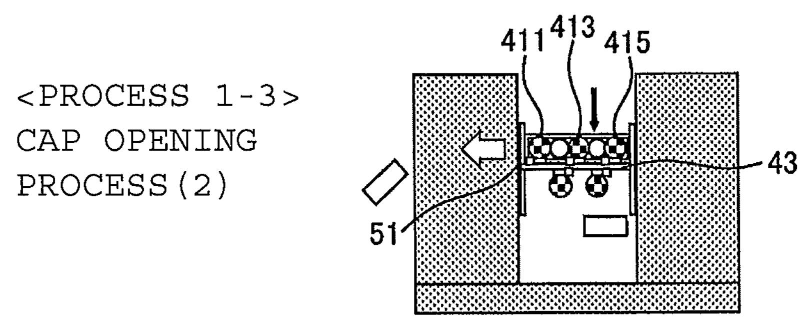
FIG. 4C is the diagram of the movement pattern ranging from the carrying-in of the first sample container to the process of opening the cap thereof according to the first embodiment of the present invention.

With the chuck mechanisms 412 and 414 holding the caps 72 and 74, the transport arm 43 of the chuck mechanism 41 in the opening/closing unit 4 moves in the Y direction to bring the remaining sample containers capped with their caps to a position where the opening/closing unit 4 can perform the cap opening process. The chuck mechanisms (411, 413, 415) of the opening/closing unit 4 open the caps (71, 73, 75) of the sample containers (61, 63, 65) on the rack 51. The removed caps (71, 73, 75) are held by the chuck mechanisms (411, 413, 415) (FIG. 4C).

(Process 1-4)

Figure 4D:
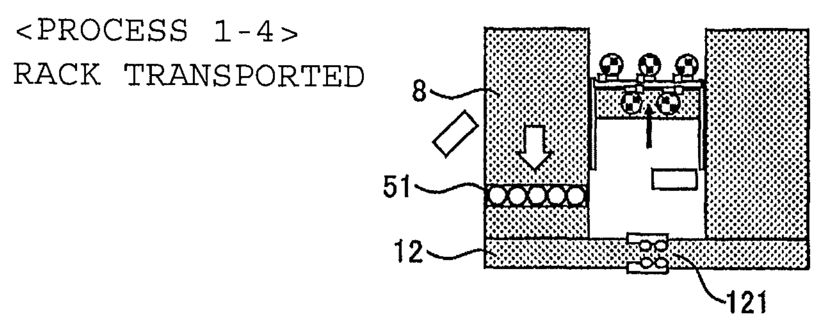
FIG. 4D is the diagram of the movement pattern ranging from the carrying-in of the first sample container to the process of opening the cap thereof according to the first embodiment of the present invention.

The rack 51 carrying the opened sample containers (61-65) is transported by the slide mechanism of the transport unit 8 from the transfer line 451 back to the first transport line 83. Thereafter, the rack 51 is transported to the sample collection position on the sample line 12 (FIG. 4D).

(Process 1-5)

Figure 4E:
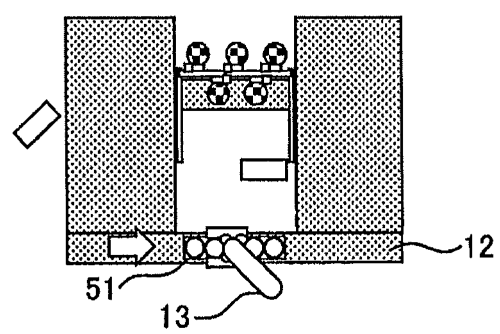
FIG. 4E is a diagram of a movement pattern ranging from the dispensing of the first sample container to the process of closing the cap thereof according to the first embodiment of the present invention.

The sample probes 13 perform the dispensing process on each of the samples (61-65) (FIG. 4E).

(Process 1-6)

Figure 4F:
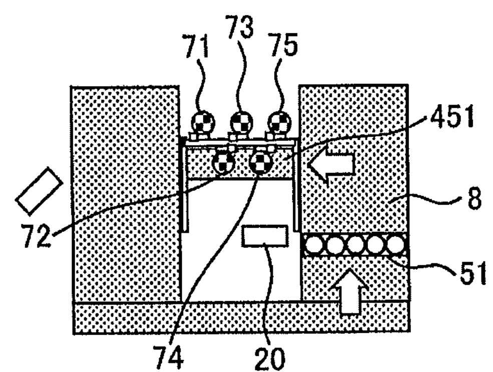
FIG. 4F is the diagram of the movement pattern ranging from the dispensing of the first sample container to the process of closing the cap thereof according to the first embodiment of the present invention.

The rack 51 on which the dispensing process has ended is moved from the sample line 12 to the second transport line. Thereafter, the rack 51 is transferred to the cap opening/closing position where the cap opening process was performed in processes 1-1 through 1-3 above. Whether or not the transfer line 451 is allowed to accept the rack 5 is determined by the ID reading unit 20 and by the control computer 200, not shown. In this determination process, the ID reading unit 20 identifies the sample information and queries the sample information management unit 202 of the control computer 200. The control computer 200 determines whether or not to transfer the sample containers in question to the opening/closing unit 4 by referencing the status of the unit 4 (whether the opening/closing unit 4 is performing the cap opening or closing process on other sample containers, whether the unit 4 is holding the caps of sample containers other than those of interest, etc.). Based on the result of the determination, the transport unit 8 transports the sample containers to the transfer line 451 or causes them to wait on the first transport line 83. The rack 51 allowed to be accepted from the second transport line 84 onto the transfer line 451 is transported to the opening/closing position where the original caps (71-75) are being held (FIG. 4F).

(Process 1-7)

Figure 4G:
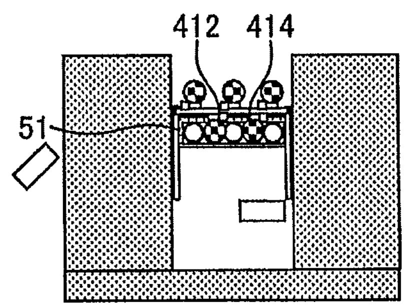
FIG. 4G is the diagram of the movement pattern ranging from the dispensing of the first sample container to the process of closing the cap thereof according to the first embodiment of the present invention.

After the sample containers are accepted onto the transfer line 451, the sample containers (62, 64) on the rack 51 are capped with the caps (52, 54) held by the chuck mechanisms (412, 414) of the opening/closing unit 4 (FIG. 4G).

(Process 1-8)

Figure 4H:
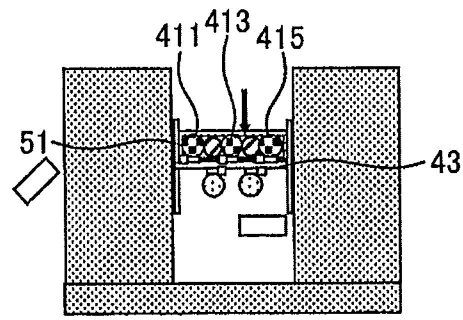
FIG. 4H is the diagram of the movement pattern ranging from the dispensing of the first sample container to the process of closing the cap thereof according to the first embodiment of the present invention.

The transport arm 43 of the chuck mechanism 41 in the opening/closing unit 4 moves in the Y direction to bring the remaining uncapped sample containers to the position where the cap closing process can be performed. The sample containers (61, 63, 65) on the rack 51 are capped with the caps (51, 53, 55) held by the chuck mechanisms (411, 413, 415) of the opening/closing unit 4 (FIG. 4H).

(Process 1-9)

Figure 4I:
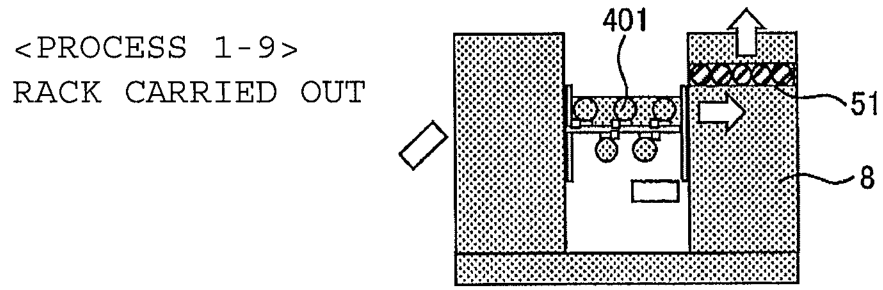
FIG. 4I is a diagram of a movement pattern involving the process of carrying out the first sample container and the process of carrying in a second sample container according to the first embodiment of the present invention.

When the cap closing process is completed on all sample containers (61-65) mounted on the rack 51, the rack 51 is transported from the transfer line 451 back to the second transport line 83 (FIG. 4I).

(Process 2-1)

Figure 4J:
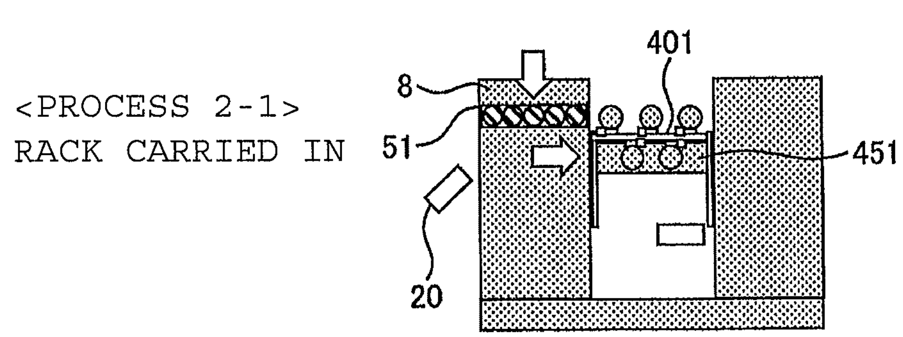
FIG. 4J is the diagram of the movement pattern involving the process of carrying out the first sample container and the process of carrying in the second sample container according to the first embodiment of the present invention.

When the rack 51 is discharged from the transfer line 451 onto the second transport line 83, the next rack 52 that needs to undergo the cap opening process is transferred from the first transport line to the transfer line 451. The transfer line 451 (i.e., cap opening/closing position) is determined by the ID reading unit 20 and by the control computer 200, not shown (FIG. 4J). The operations above are repeated thereafter.

Second Embodiment

Figure 3D:
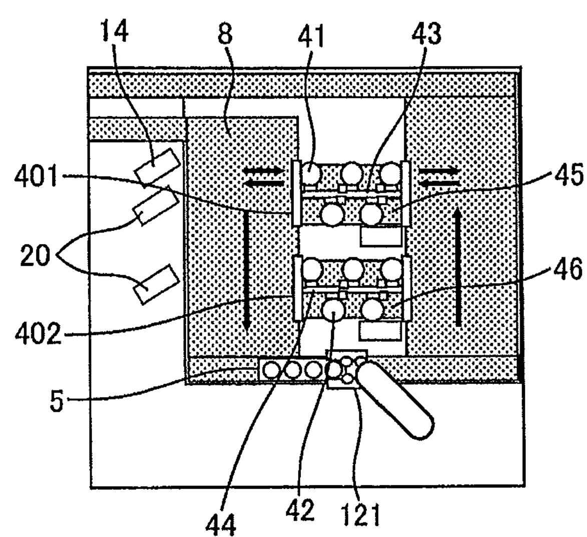
FIG. 3D is a schematic view showing a structure of an opening/closing unit according to a second embodiment of the present invention.
Figure 3E:
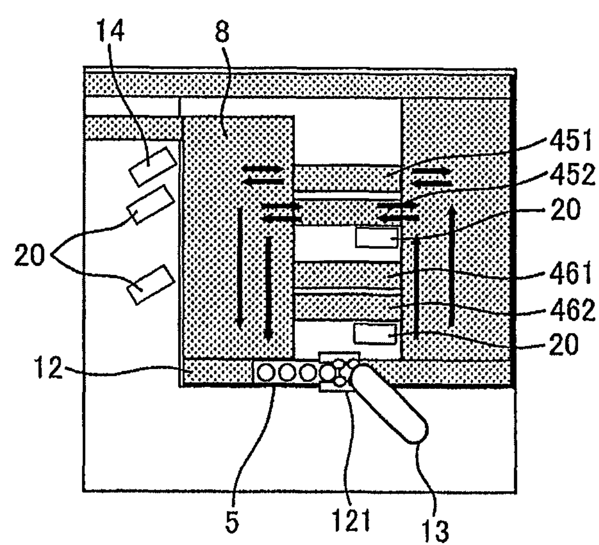
FIG. 3E is a schematic view showing a structure of a transport unit according to the second embodiment of the present invention.

FIGS. 3D and 3E show the second embodiment. In conjunction with the second embodiment, there will be explained a case where two transfer lines serving as the third transport line are provided for one opening/closing unit.

Prior to analysis, the automatic analysis system is subjected to maintenance. Maintenance work typically involves inspecting the optical detector 17, cleaning the reaction vessels 9, and cleaning various probes such as the sample probes 13. Thereafter, samples serving as the test object such as blood or urine are sealed into the sample containers 6 which, still capped with the caps, are placed onto the rack 5 and transferred by the transport unit 8.

The sample information identification unit 14 installed around the transport unit 8 reads sample information to identify each sample container 6 (in diameter, height, and type). The sample information identification unit 14 also determines the presence or absence of the cap 7 of each sample container 6 and identifies the type of each cap 7 (rubber cap, plastic guard cap, screw cap, etc.) at the same time. The sample information identification unit 14 images the sample containers 6 to acquire their images and analyzes the acquired images to determine the opened/closed state of the sample containers 6 (i.e., presence or absence of their caps 7) and identify the type of each cap 7. In this manner, the types and attributes of the sample containers 6 and their caps 7 are stored into the storage unit 201 inside the control computer 200 as the information regarding the sample containers 6 together with the date of acceptance of each sample, the acceptance number of the sample, attribute of the patient involved, etc. Based on the stored information, the sample information management unit 202 inside the control computer 200 determines whether the processes of opening and closing each sample container 6 are possible, and performs other processes as well.

The sample information management unit 202 in the control computer 200 determines the processing details of each sample (whether its container is opened or not, and the destination of the rack 5) based on the analyzed information. In this respect, the processing details of each sample may be determined alternatively based on information coming from the host control computer 200. On the basis of the identification process that involved reading of the information as described above, the destination of the rack 5 is determined (i.e., the position where the caps are opened by the opening/closing unit 401 or by the opening/closing unit 402).

Incidentally, the sample information management unit 202 stores beforehand the information necessary for the opening and closing of caps (torque, operating conditions, and conditions for determining anomaly) in a manner fit for the type of the sample containers 6 (e.g., blood collection tube). If a plurality of opening/closing units are provided, the information about the use status of these units may also be stored in advance. The use status of the opening/closing units includes information as to whether the cap opening process and cap closing process are carried out and whether the removed caps are being retained.

Next, the ID reading unit 20 performs the process of identifying the rack 5 and sample containers 6. The ID reading unit 20 reads sample identifying information such as sample IDs from RFID tags or sample barcodes pasted on the rack 5 and sample containers 6. The sample identifying information thus read is transmitted to the sample information management unit 202 inside the control computer 200 and registered therein along with the information about the opening/closing unit 4 performing the cap opening process, about the identity of the sample containers 6 (in diameter, height, and type), about the presence or absence of the caps 7, and about the cap types (rubber cap, plastic guard cap, screw cap, etc.).

The rack 5 on which the sample containers 6 were identified by the ID reading unit 20 is transferred to the cap opening/closing units (401, 402). Given the identification of the sample containers 6 read by the sample information identification unit 14, optimal operating conditions for the opening/closing unit 4 are determined in accordance with the conditions registered in the sample information management unit 202. Based on the operating conditions thus determined, the opening/closing units (401, 402) perform the cap opening process. In keeping with the information from RFID tags on which the sample information is registered or with the information from sample barcodes, the cap opening/closing unit 4 recognizes the type of each cap 7 and opens it accordingly. The caps 7 thus opened are retained by the cap opening/closing unit 4. The processes of opening and closing the caps 7 will be discussed later in detail.

The sample containers 6 with their caps 7 removed are transferred to the sample line 12 by the transport unit 8. The sample containers 6 transferred onto the sample line 12 are transported to the sample collection position where the sample probes 13 perform the sample dispensing process. The samples collected by the sample probes 13 are dispensed by a predetermined amount into the reaction vessels 9 arranged on the reaction disk 2. A predetermined amount of reagent is dispensed into the reaction vessels 9 after being taken from the reagent vessels 11 by the reagent probe 10. The stirring unit 15 stirs the reaction vessels 9 for a predetermined time period for reaction purposes, before the optical detector 17 measures the samples in the reaction vessels 9 for absorbance, spectrum, etc. The results of the measurement are output to the control computer 200, not shown. Where further items of measurement are requested, the sample dispensing operations described above are repeated for each of the items. The sample dispensing process is repeated likewise until it is complete when all predetermined measurement items for the samples in all sample containers 6 on the rack 5 have been dealt with.

The rack 5 on which the sample dispensing process is completed is transferred back to the opening/closing position of the opening/closing unit 4 that has performed the cap opening process. The ID reading unit 20 reads the information of the rack 5 carrying the dispensed sample containers 6 so as to determine the cap opening/closing unit that should perform the cap closing process.

Since the opening/closing unit that has carried out the cap opening process retains and manages the caps 7 removed from the sample containers 6, the sample containers 6 transferred to the opening/closing position of the same opening/closing unit that has removed the caps 7 are then capped thereby with the same caps removed before the dispensing process. The sample containers 6 with their caps 7 attached again are transferred by the transport unit 8 to the sample holding unit, not shown.

FIG. 3E is a schematic view in which the chuck mechanisms (41, 42) of the cap opening/closing units (401, 402) and the transport arms (43, 44) are not shown. The transport lines A 45 and B 46 serving as the third transport line for the rack 5 are equipped respectively with a transfer line A (45) composed of a pair of transfer lines 451 and 452 and with a transfer line B (46) made up of a pair of transfer lines 461 and 462. The transfer line A 45 composed of the transfer lines 451 and 452 is a transfer line on which the opening/closing process is performed by the first opening/closing unit 401, and the transfer line B 46 made up of the transfer lines 461 and 462 is a transfer line on which the opening/closing process is carried out by the second opening/closing unit 402.

FIGS. 8A through 8F show the operating procedure of the cap opening process and cap closing process performed by the second embodiment.

(Opening/Closing Process 1)

Figure 8A:
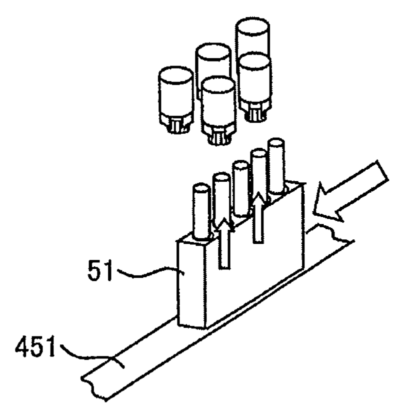
FIG. 8A is a diagram of a movement pattern involving the processes of opening and closing the caps of sample container according to the second embodiment of the present invention.

Upon completion of the dispensing process, the rack 51 on which the cap opening process needs to be performed is transported to the opening/closing position on the transfer line 451 (FIG. 8A). The transport arm 43, not shown, moves in the three axial directions to bring the chuck mechanisms 411 through 415 to a position fit for closing the caps of the sample containers 61 through 65 mounted on the rack 51. The transport arm waits after the cap closing position is reached (FIG. 8A).

(Opening/closing process 2)

Figure 8B:
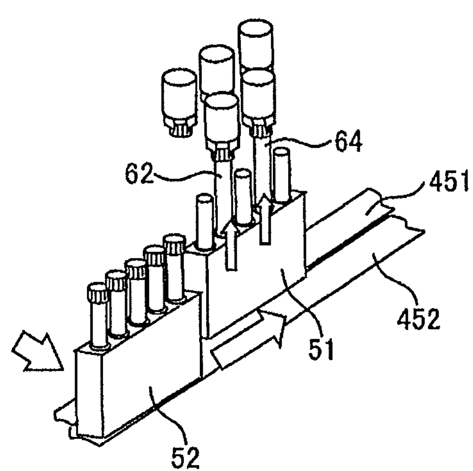
FIG. 8B is the diagram of the movement pattern involving the processes of opening and closing the caps of sample container according to the second embodiment of the present invention.

Of the five sample containers mounted on the rack 51, the sample containers (62, 64) are first subjected to the cap closing process. The sample containers 62 and 64 are lifted to the predetermined height by the sample container clamping mechanism, not shown. At this point, a rack 52 which is different from the rack 51 and on which the cap opening process needs to be performed is transported from the transport unit 8 to the transfer line 452 adjacent to the transfer line 451 (FIG. 8B).

(Opening/Closing Process 3)

The chuck mechanisms (412, 414) holding caps clutch the sample containers (62, 64) mounted on the rack 51 and perform a suitable cap closing process on the sample containers (62, 64) according to the type of the caps being held.

Figure 8C:
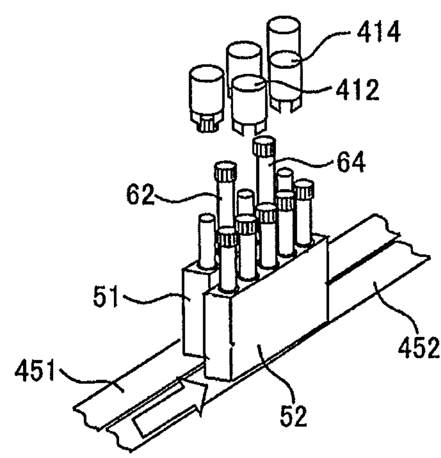
FIG. 8C is the diagram of the movement pattern involving the processes of opening and closing the caps of sample container according to the second embodiment of the present invention.

In this case, the sample containers (62, 64) are capped with their original caps (72, 74) removed before the dispensing process. At this point, the rack 52 is brought to the opening/closing position on the transfer line 452 (FIG. 8C).

(Opening/Closing Process 4)

Figure 8D:
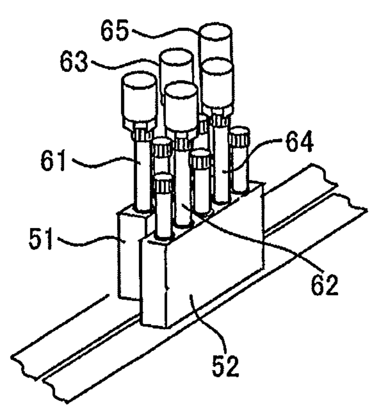
FIG. 8D is the diagram of the movement pattern involving the processes of opening and closing the caps of sample container according to the second embodiment of the present invention.

The remaining sample containers (61, 63, 65) on the rack 51 are lifted to the predetermined height by the sample containing clamping mechanism, not shown. Also, the sample containers (62, 64) on the rack 52 are lifted to the predetermined height by the sample container clamping mechanism, not shown (FIG. 8D).

(Opening/Closing Process 5)

Figure 8E:
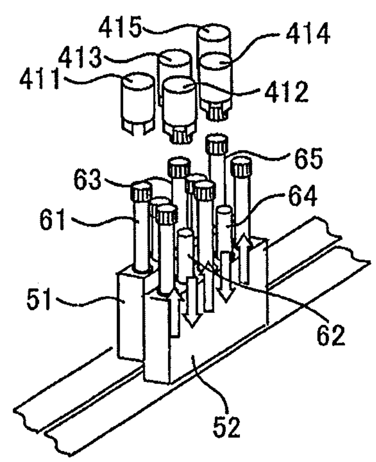
FIG. 8E is the diagram of the movement pattern involving the processes of opening and closing the caps of sample container according to the second embodiment of the present invention.
Figure 8F:
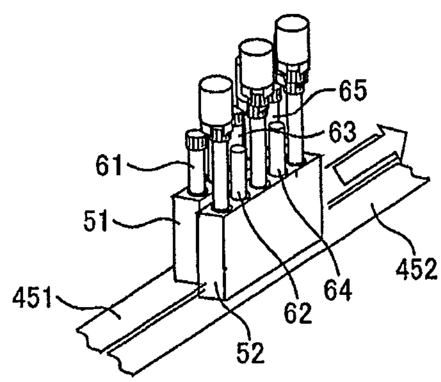
FIG. 8F is the diagram of the movement pattern involving the processes of opening and closing the caps of sample container according to the second embodiment of the present invention.

The caps (71, 73, 75) held by the chuck mechanisms (411, 413, 415) are attached to the sample containers (61, 63, 65) on the rack 51 by a suitable method according to the cap type. Also, the chuck mechanisms (412, 414) open the caps (72, 74) of the sample containers (62, 64) on the rack 52 using a suitable cap opening method according to the cap type. The chuck mechanisms 412 and 414 hold the removed caps (FIG. 8E).

(Opening/Closing Process 6)

The sample containers (61, 63, 65) on the rack 51 of which the cap opening process has ended on all mounted sample containers are lowered to the installation position of the rack 5 by the sample container clamping mechanism, not shown. The rack 51 is transported from the transfer line 451. Also, the sample containers (62, 64) on the rack 52 are lowered by the sample container clamping mechanism, not shown. Thereafter, the sample containers (61, 63, 65) which are mounted on the rack 52 and on which the cap opening process has yet to be completed are lifted to the predetermined height by the sample container clamping mechanism, not shown. The cap opening process is performed on the sample containers in the same manner as described above (FIG. 8F).

FIGS. 5A through 5T and FIGS. 6A and 6B show the rack movement patterns ranging from the cap opening process to the cap closing process involving the use of the cap opening/closing unit 4 structured as discussed above.

FIG. 5 depicts the operation patterns involved, showing how the second embodiment is practiced. Opening patterns are shown in FIG. 5A to FIG. 5T. Here, processes 1-1 through 1-9 are performed on the first rack 51, processes 2-1 through 2-9 on the second rack 52, and process 3-1 and the subsequent processes on a third rack 53. It should be noted that the operations shown in FIGS. 5A through 5F (of processes 1-1 through 1-6) are the same as those on the transfer line 451 in FIGS. 4A through 4F.

(Process 1-1)

Figure 5A:
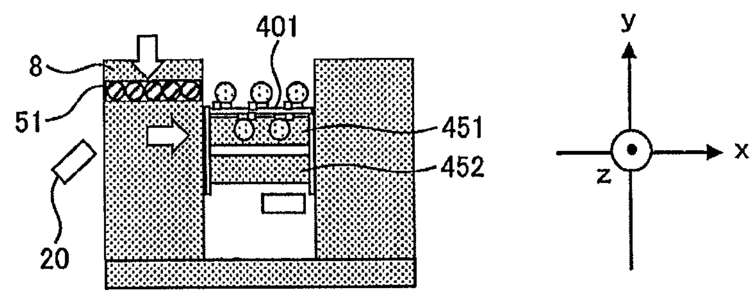
FIG. 5A is a diagram of a movement pattern ranging from the carrying-in of the first sample container to the process of opening the cap thereof according to the second embodiment of the present invention.

The rack 51 transported to the first transport line 83 by way of the supply line 81 is transported to the transfer line 451 or transfer line 452 of the opening/closing unit 4. Which of the transfer lines the rack 51 is transported to is determined by the ID reading unit 20 and control computer 200 (FIG. 5A). In this determination process, the ID reading unit 20 identifies the sample information and queries the sample information management unit 202 of the control computer 200. The control computer 200 determines whether or not to transfer the sample containers in question by referencing the status of the opening/closing unit 401 and referencing that of the transfer lines 451 and 452 (whether the opening/closing unit 4 is performing the cap opening or closing process on other sample containers, whether the unit 4 is holding the caps of sample containers other than those of interest, whether another rack is currently on the transfer line (451, 452), etc.). Based on the result of the determination, the transport unit 8 transports the sample containers to the transfer line 451 or transfer line 452 or causes them to wait on the first transport line 83. With this embodiment, the ensuing explanation will be based on the assumption that the sample rack is carried onto the transfer line 451.

(Process 1-2)

Figure 5B:
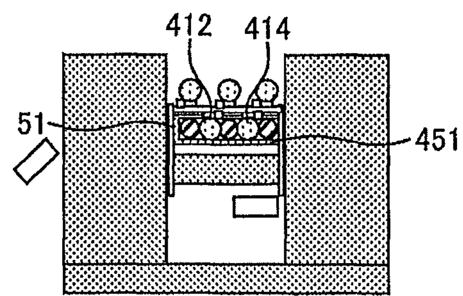
FIG. 5B is the diagram of the movement pattern ranging from the carrying-in of the first sample container to the process of opening the cap thereof according to the second embodiment of the present invention.

The chuck mechanisms (412, 414) of the opening/closing unit 4 open the caps (72, 74) of the sample containers (62, 64) on the rack 51. The removed caps (72, 74) are retained by the chuck mechanisms (412, 414) (FIG. 5B).

(Process 1-3)

Figure 5C:
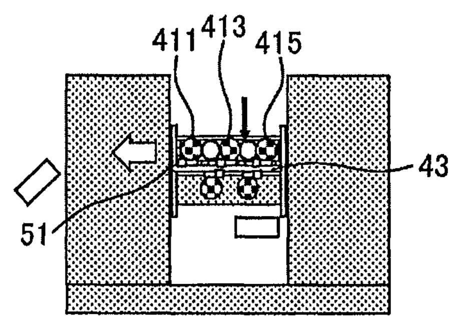
FIG. 5C is the diagram of the movement pattern ranging from the carrying-in of the first sample container to the process of opening the cap thereof according to the second embodiment of the present invention.

With the chuck mechanisms 412 and 414 holding the caps 72 and 74, the transport arm 43 of the chuck mechanism 41 in the opening/closing unit 4 moves in the Y direction to bring the remaining sample containers with their caps yet to be removed to the position where these sample containers are subjected to the cap opening process by the opening/closing unit 4. The chuck mechanisms 411, 413 and 415 of the opening/closing unit 4 open the caps (71, 73, 75) of the sample containers (61, 63, 65) on the rack 51. The removed caps (71, 73, 75) are retained by the chuck mechanisms (411, 413, 415) (FIG. 5C).

(Process 1-4)

Figure 5D:
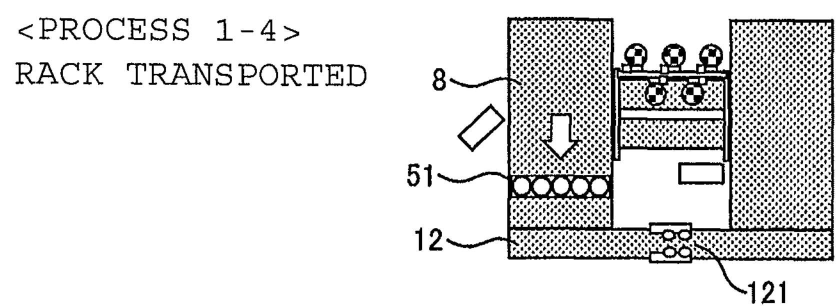
FIG. 5D is the diagram of the movement pattern ranging from the carrying-in of the first sample container to the process of opening the cap thereof according to the second embodiment of the present invention.

The rack 51 on which all sample containers have had their caps opened is transported from the transfer line 451 back to the first transport line 83 by the slide mechanism of the transport unit 8, before being carried onto the sample line 12 and transported up to the sample dispensing position on the sample line (FIG. 5D).

(Process 1-5)

Figure 5E:
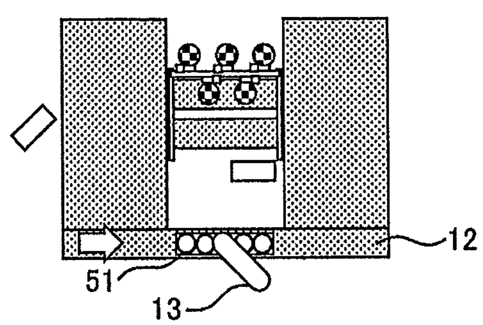
FIG. 5E is a diagram of a movement pattern ranging from the dispensing of the first sample container to the process of closing the cap thereof, and the process of carrying in the second sample container according to the second embodiment of the present invention.

The sample probes 13 perform the dispensing process on the samples (61-65) (FIG. 5E).

(Process 1-6)

Figure 5F:
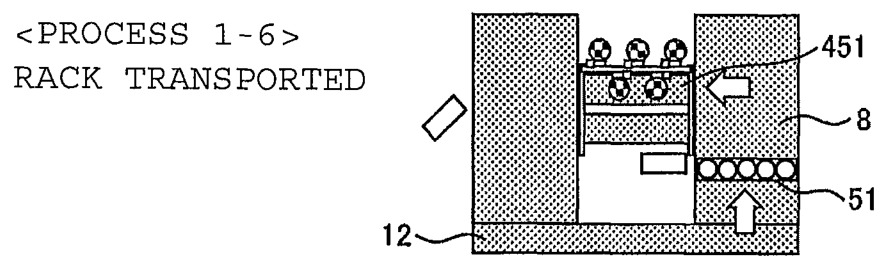
FIG. 5F is the diagram of the movement pattern ranging from the dispensing of the first sample container to the process of closing the cap thereof, and the process of carrying in the second sample container according to the second embodiment of the present invention.

The rack 51 on which the dispensing process has ended is transported from the sample line 12 to the second transport line 84. Thereafter, the rack 51 is transferred to the position where the cap closing process may be performed by the same opening/closing unit 4 that carried out the cap opening process in processes 1-1 through 1-3 above. With this embodiment, there are two transfer lines 451 and 452 that can be accessed by the opening/closing unit 4. Which of the transfer lines is to be used for the cap closing process is determined by a sample information identification mechanism disposed on the sample line and by the control computer 200. In this determination process, the ID reading unit 20 identifies the sample information of the sample containers on which the dispensing process has ended, and queries the control computer 200. The control computer 200 identifies the same opening/closing unit 401 that carried out the cap opening process in processes 1-1 through 1-3 above by referencing the information recorded in the sample information management unit 202. The control computer 200 further determines whether or not to transfer the sample containers in question by referencing the status of the opening/closing unit 401 and that of the transfer lines 451 and 452 (whether the opening/closing unit 4 is performing the cap opening or closing process on other sample containers, whether the unit 4 is holding the caps of sample containers other than those of interest, whether another rack is currently on the transfer line 451 or 452, etc.). Based on the result of the determination, the transport unit 8 transports the sample containers to the transfer line 451 or transfer line 452 or causes them to wait on the second transport line 84. With this embodiment, it is assumed that the sample rack is allowed to be transported to the transfer line 451. The rack 51 in question is transported to the opening/closing position where the original caps (71 through 75) are being held (FIG. 5F).

(Process 1-7)

The caps (52, 54) held by the chuck mechanism of the opening/closing unit 4 are attached to the sample containers (62, 64) on the rack 51.

(Process 2-1)

Figure 5G:
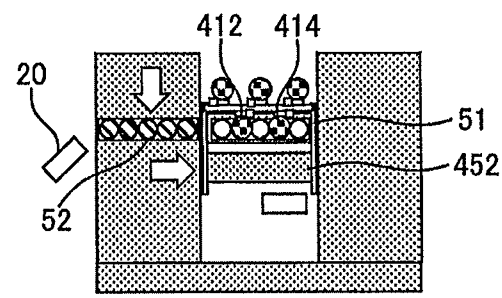
FIG. 5G is the diagram of the movement pattern ranging from the dispensing of the first sample container to the process of closing the cap thereof, and the process of carrying in the second sample container according to the second embodiment of the present invention.

At the same timing as process 1-7, the second rack 52 subject to another cap opening process is transported to the first transport line by way of the supply line 81 and transferred to the transfer line 452 where the cap opening process may be carried out by the opening/closing unit 4. The transfer line 452 (i.e., cap opening/closing position) is determined by the ID reading unit 20 and by the control computer 200, not shown. In this determination process, the ID reading unit 20 identifies the information of the second rack 52 and queries the sample information management unit 202 of the control computer 200. The control computer 200 determines whether or not to transfer the sample containers in question by referencing the information recorded in the information management unit 202 and referencing the status of the opening/closing unit 401 and that of the transfer lines 451 and 452 (whether the opening/closing unit 401 is performing the cap opening or closing process on other sample containers, whether the unit 401 is holding the caps of sample containers other than those of interest, whether another rack is currently on the transfer line 451 or 452, etc.). Based on the result of the determination, the transport unit 8 transports the sample containers to the transfer line 451 or transfer line 452 or causes them to wait on the second transport line 84. With this embodiment, the rack 51 is currently subjected to the cap closing process on the transfer line 451, so that the control computer 200 permits the rack 52 to be transported to the transfer line 452 (FIG. 5G).

(Process 1-8)

The transport arm 43 of the chuck mechanism 41 in the opening/closing mechanism moves in the Y direction to attach the caps (51, 53, 55) held by the chuck mechanisms (411, 413, 415) of the opening/closing unit 4 to the sample containers (61, 63, 65) on the rack 51.

(Process 2-2)

Figure 5H:
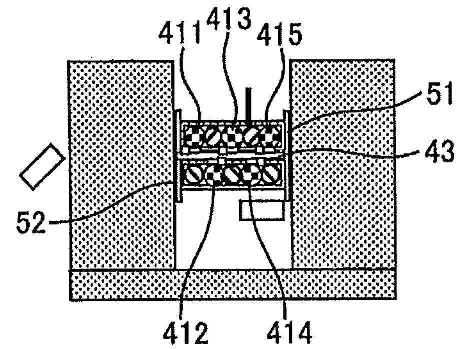
FIG. 5H is the diagram of the movement pattern ranging from the dispensing of the first sample container to the process of closing the cap thereof, and the process of carrying in the second sample container according to the second embodiment of the present invention.

At the same time as process 1-8, the chuck mechanisms (412, 414) of the opening/closing unit 4 open the caps (72, 74) of the sample containers (62, 64) on the second rack 52. The removed caps (72, 74) are retained by the chuck mechanisms (412, 414) (FIG. 5H).

(Process 1-9)

When the cap closing process has ended on all sample containers (61-65) mounted on the rack 51, the rack 51 is discharged from the transfer line 451 back to the second transport line 84.

(Process 2-3)

Figure 5I:
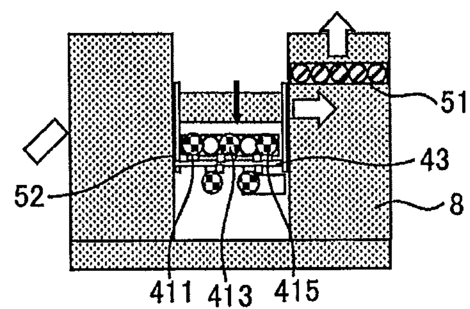
FIG. 5I is a diagram of a movement pattern involving the process of carrying out the first sample container, and ranging from the opening of the cap of the second sample container to the process of dispensing of the second sample container according to the second embodiment of the present invention.

At the same time as process 1-9, the transport arm 43 of the chuck mechanism 41 in the opening/closing unit 4 moves in the Y direction to bring the remaining sample containers with their caps yet to be opened on the rack 52 to the position where the cap opening process may be performed by the opening/closing unit 4. The chuck mechanisms (411, 413, 415) of the opening/closing unit 4 perform the cap opening process on the caps (71, 73, 75) of the sample containers (61, 63, 65) on the rack 52. The removed caps (71, 73, 75) are retained by the chuck mechanisms (411, 413, 415) (FIG. 5I).

(Process 2-4)

Figure 5J:
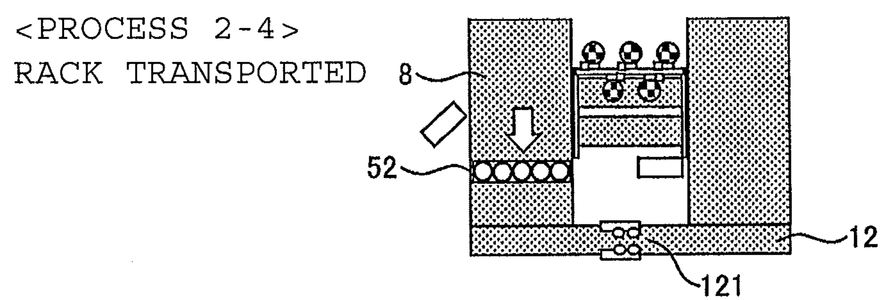
FIG. 5J is the diagram of the movement pattern involving the process of carrying out the first sample container, and ranging from the opening of the cap of the second sample container to the process of dispensing of the second sample container according to the second embodiment of the present invention.

The rack 52 on which all sample containers (61-65) have had their caps (71-75) opened is transferred from the transfer line 452 back to the first transport line 83, before being transported to the sample collection position on the sample line 12 (FIG. 5J).

(Process 2-5)

Figure 5K:
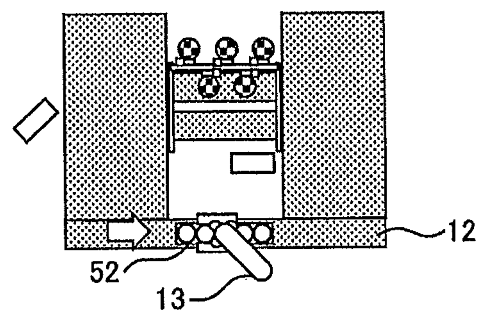
FIG. 5K is the diagram of the movement pattern involving the process of carrying out the first sample container, and ranging from the opening of the cap of the second sample container to the process of dispensing of the second sample container according to the second embodiment of the present invention.

The sample probes 13 perform the dispensing process on the samples (61-65) (FIG. 5K).

(Process 2-6)

Figure 5L:
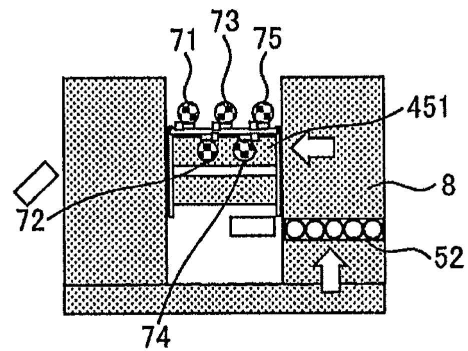
FIG. 5L is the diagram of the movement pattern involving the process of carrying out the first sample container, and ranging from the opening of the cap of the second sample container to the process of dispensing of the second sample container according to the second embodiment of the present invention.

The rack 52 on which the dispensing of the samples has ended is transported from the sample line 12 to the second transport line 84. Thereafter, the rack 52 is transported to the position where the cap closing process may be performed by the same opening/closing unit 4 that carried out the cap opening process in processes 2-1 through 2-3 above. With this embodiment, there are two transfer lines 451 and 452 that can be accessed by the opening/closing unit 4. Which of the transfer lines is to be used for the cap closing process is determined by the sample information identification unit 14 disposed on the sample line and by the control computer 200. In this determination process, the ID reading unit 20 identifies the sample information of the sample containers on which the dispensing process has ended, and queries the control computer 200. The control computer 200 identifies the same opening/closing unit 401 that carried out the cap opening process in processes 2-1 through 2-3 above by referencing the information recorded in the sample information management unit 202. The control computer 200 further determines whether or not to transfer the sample containers in question by referencing the status of the opening/closing unit 401 and that of the transfer lines (451, 452) (whether the opening/closing unit 4 is performing the cap opening or closing process on other sample containers, whether the unit 4 is holding the caps of sample containers other than those of interest, whether another sample rack is currently on the transfer line (451, 452), etc.). Based on the result of the determination, the transport unit 8 transports the sample containers to the transfer line 451 or transfer line 452 or causes them to wait on the second transport line 84. With this embodiment, it is assumed that the sample rack is allowed to be transported to the transfer line 451. It is also assumed for this embodiment that an instruction is given to transport the rack 52 to the transfer line 451 for the cap closing process to be performed by the opening/closing unit 401 retaining the original caps (71-75) (FIG. 5L).

(Process 2-7)

The caps (72, 74) held by the chuck mechanisms (412, 414) of the opening/closing unit 4 are attached to the sample containers (62, 64) on the rack 52.

(Process 3-1)

Figure 5M:
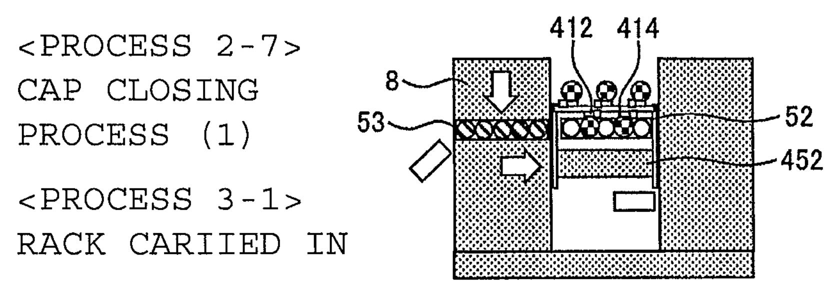
FIG. 5M is a diagram of a movement pattern ranging from the closing of the cap of the second sample container to the process of carrying out the second sample container, and ranging from the carrying-in of a third sample container to the process of opening the cap thereof according to the second embodiment of the present invention.

At the same timing as process 2-7, the next rack 53 subject to another cap opening process is transported to the first transport line 83 by way of the supply line 81, before being transferred onto the transfer line 452 where the cap opening process may be performed by the opening/closing unit 4. The transfer line 452 (i.e., cap opening/closing position) is determined by the ID reading unit 20 and by the control computer 200, not shown. In this determination process, the ID reading unit 20 identifies the sample information of the third rack 53, and queries the sample information management unit 202 of the control computer 200. The control computer 200 determines whether or not to transfer the sample containers in question by referencing the information recorded in the information management unit 202 and referencing the status of the opening/closing unit 401 and that of the transfer lines (451, 452) (whether the opening/closing unit 401 is performing the cap opening or closing process on other sample containers, whether the unit 401 is holding the caps of sample containers other than those of interest, whether another sample rack is currently on the transfer line (451, 452), etc.). Based on the result of the determination, the transport unit 8 transports the sample containers to the transfer line 451 or transfer line 452 or causes them to wait on the first transport line 83. With this embodiment, the control computer 200 permits the rack 52 to be transported to the transfer line 452 because the rack 51 is undergoing the cap closing process on the transfer line 451. With this embodiment, the sample containers are transported to the transfer line 452 because the rack 52 is undergoing the cap closing process on the transfer line 451 (FIG. 5M).

(Process 2-8)

The transport arm 43 of the chuck mechanism 41 in the opening/closing mechanism moves in the Y direction to attach the cap (71, 73, 75) held by the chuck mechanisms (411, 413, 415) of the opening/closing unit 4 to the sample containers (61, 63, 65) on the rack 52.

(Process 3-2)

Figure 5N:
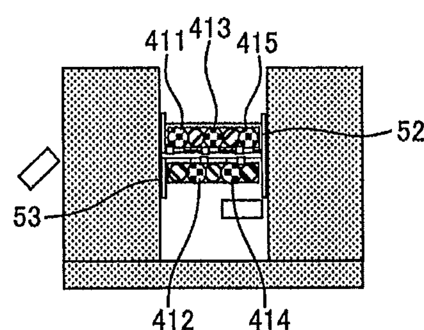
FIG. 5N is the diagram of the movement pattern ranging from the closing of the cap of the second sample container to the process of carrying out the second sample container, and ranging from the carrying-in of the third sample container to the process of opening the cap thereof according to the second embodiment of the present invention.

At the same time as process 2-8, the chuck mechanisms (412, 414) of the opening/closing unit 4 open the caps (72, 74) of the sample containers (62, 64) on the rack 53. The removed caps (52, 54) are retained by the chuck mechanisms (412, 414) (FIG. 5N).

(Process 2-9)

When the cap closing process has ended on all sample containers (61, 63, 65) mounted on the rack 52, the rack 52 is discharged from the transfer line 451 back to the second transport line.

(Process 3-3)

Figure 5O:
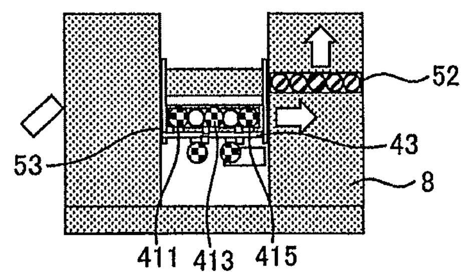
FIG. 5O is the diagram of the movement pattern ranging from the closing of the cap of the second sample container to the process of carrying out the second sample container, and ranging from the carrying-in of the third sample container to the process of opening the cap thereof according to the second embodiment of the present invention.

At the same time as process 2-9, the transport arm 43 of the chuck mechanism 41 in the opening/closing unit 4 moves. The chuck mechanism 41 of the opening/closing unit 4 opens the caps (71, 73, 75) of the sample containers (61, 63, 65) on the rack 53. The removed caps (71, 73, 75) are retained by the chuck mechanisms (411, 413, 415) (FIG. 5O).

(Process 3-4)

Figure 5P:
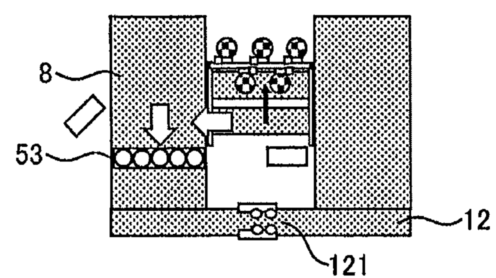
FIG. 5P is the diagram of the movement pattern ranging from the closing of the cap of the second sample container to the process of carrying out the second sample container, and ranging from the carrying-in of the third sample container to the process of opening the cap thereof according to the second embodiment of the present invention.

The rack 53 carrying the sample containers (61-65) with all their caps (71-75) opened is transferred from the transfer line 452 back to the first transport line, before being transported up to the sample dispensing position on the sample line 12 by the slide mechanism (FIG. 5P).

(Process 3-5)

Figure 5Q:
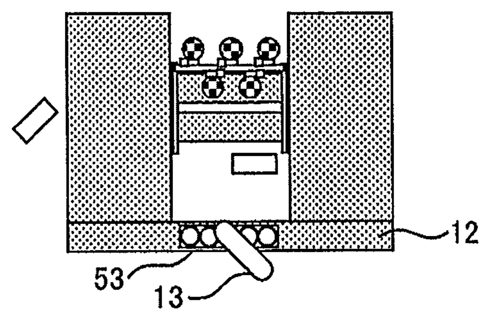
FIG. 5Q is a diagram of a movement pattern ranging from the dispensing of the third sample container to the process of closing the cap thereof, and ranging from the carrying-in of a fourth sample container to the process of opening the cap thereof according to the second embodiment of the present invention.

The sample probes 13 perform the dispensing process on the samples (61-65) (FIG. 5Q).

(Process 3-6)

Figure 5R:
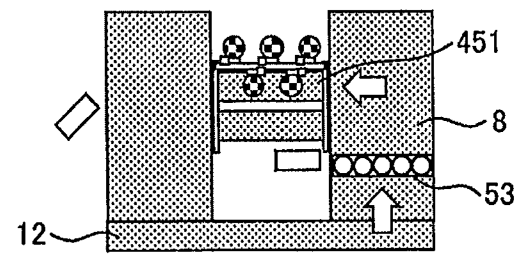
FIG. 5R is the diagram of the movement pattern ranging from the dispensing of the third sample container to the process of closing the cap thereof, and ranging from the carrying-in of the fourth sample container to the process of opening the cap thereof according to the second embodiment of the present invention.
Figure 5S:
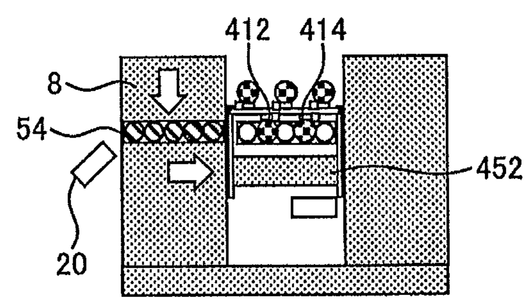
FIG. 5S is the diagram of the movement pattern ranging from the dispensing of the third sample container to the process of closing the cap thereof, and ranging from the carrying-in of the fourth sample container to the process of opening the cap thereof according to the second embodiment of the present invention.

The rack 53 on which the dispensing process has ended is transported from the sample line 12 to the second transport line 84, before being transferred by the transport unit 3 to the position where the cap closing process may be performed by the opening/closing unit 4. The transfer line 451 (i.e., cap opening/closing position) is determined by the ID reading unit 20 and by the control computer 200, not shown. In this determination process, the ID reading unit 20 identifies the sample information of the sample containers on which the dispensing process has ended, and queries the control computer 200. The control computer 200 identifies the same opening/closing unit 401 that carried out the cap opening process in processes 3-1 through 3-3 above by referencing the information recorded in the sample information management unit 202. The control computer 200 further determines whether or not to transfer the sample containers in question by referencing the status of the opening/closing unit 401 and that of the transfer lines 451 and 452 (whether the opening/closing unit 4 is performing the cap opening or closing process on other sample containers, whether the unit 4 is holding the caps of sample containers other than those of interest, whether another sample rack is currently on the transfer line 451 or 452, etc.). Based on the result of the determination, the transport unit 8 transports the sample containers to the transfer line 451 or transfer line 452 or causes them to wait on the second transport line 84. With this embodiment, it is assumed that the sample rack is allowed to be transported to the transfer line 451 because no other rack is currently on any of the transfer lines. The rack 53 is transported to the opening/closing position where the original caps (51-55) are being retained (FIG. 5R).

(Process 3-7)

The caps (52, 54) held by the chuck mechanisms (412, 414) of the opening/closing unit 4 are attached to the sample containers (62, 64) on the rack 53.

(Process 4-1)

At the same time as process 3-7, the next rack 54 that needs to undergo another cap opening process is transported to the first transport line 83 by way of the supply line 81, before being transferred to the position where the opening/closing process may be performed by the opening/closing unit 4. The transfer line 452 (i.e., cap opening/closing position) is determined by the ID reading unit 20 and by the control computer 200, not shown. The determining method is the same as what was described above regarding the racks 51 through 53 (FIG. 5S).

(Process 3-8)

Figure 5T:
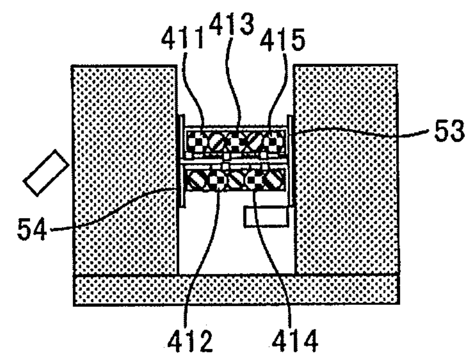
FIG. 5T is the diagram of the movement pattern ranging from the dispensing of the third sample container to the process of closing the cap thereof, and ranging from the carrying-in of the fourth sample container to the process of opening the cap thereof according to the second embodiment of the present invention.

The transport arm 43 of the chuck mechanism 41 in the opening/closing mechanism moves. The caps (71, 73, 75) held by the chuck mechanisms (411, 413, 415) of the opening/closing unit 4 are attached to the sample containers (61, 63, 65) on the rack 53. (Process 4-2) At the same time, the chuck mechanisms (412, 414) of the opening/closing unit 4 remove the caps (72, 74) of the sample containers (62, 64) on the rack 54. The removed caps (52, 54) are retained by the chuck mechanisms (412, 414) (FIG. 5T). The operations above are repeated thereafter.

Figure 6A:
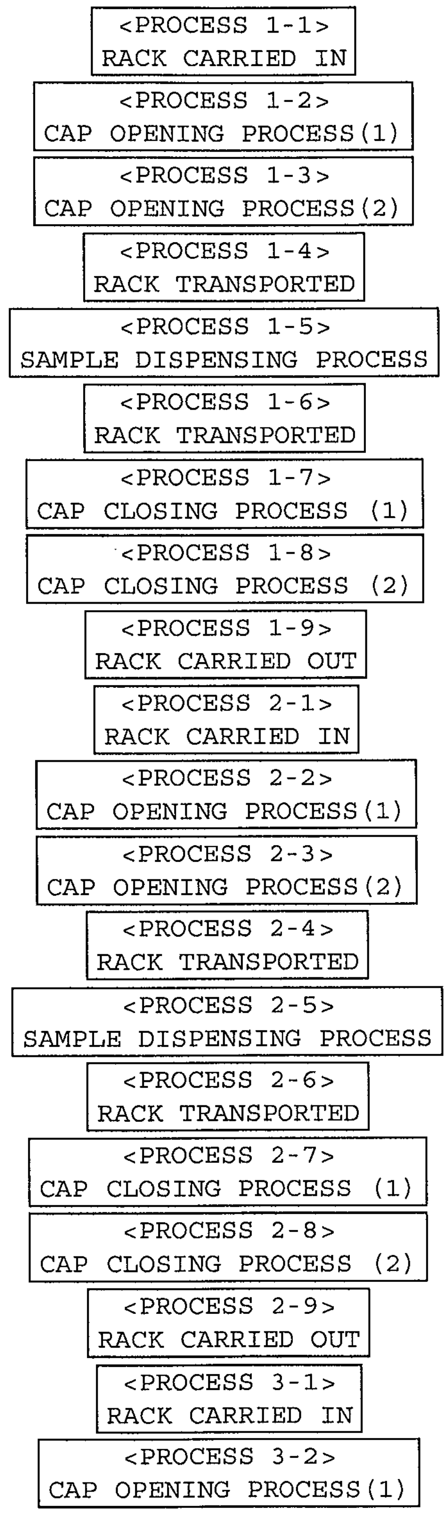
FIG. 6A is a flowchart showing operations ranging from the process of transporting sample container to the process of opening their caps, the process of dispensing of the sample container, and the process of closing their caps according to the first and the second embodiments of the present invention.
Figure 6B:
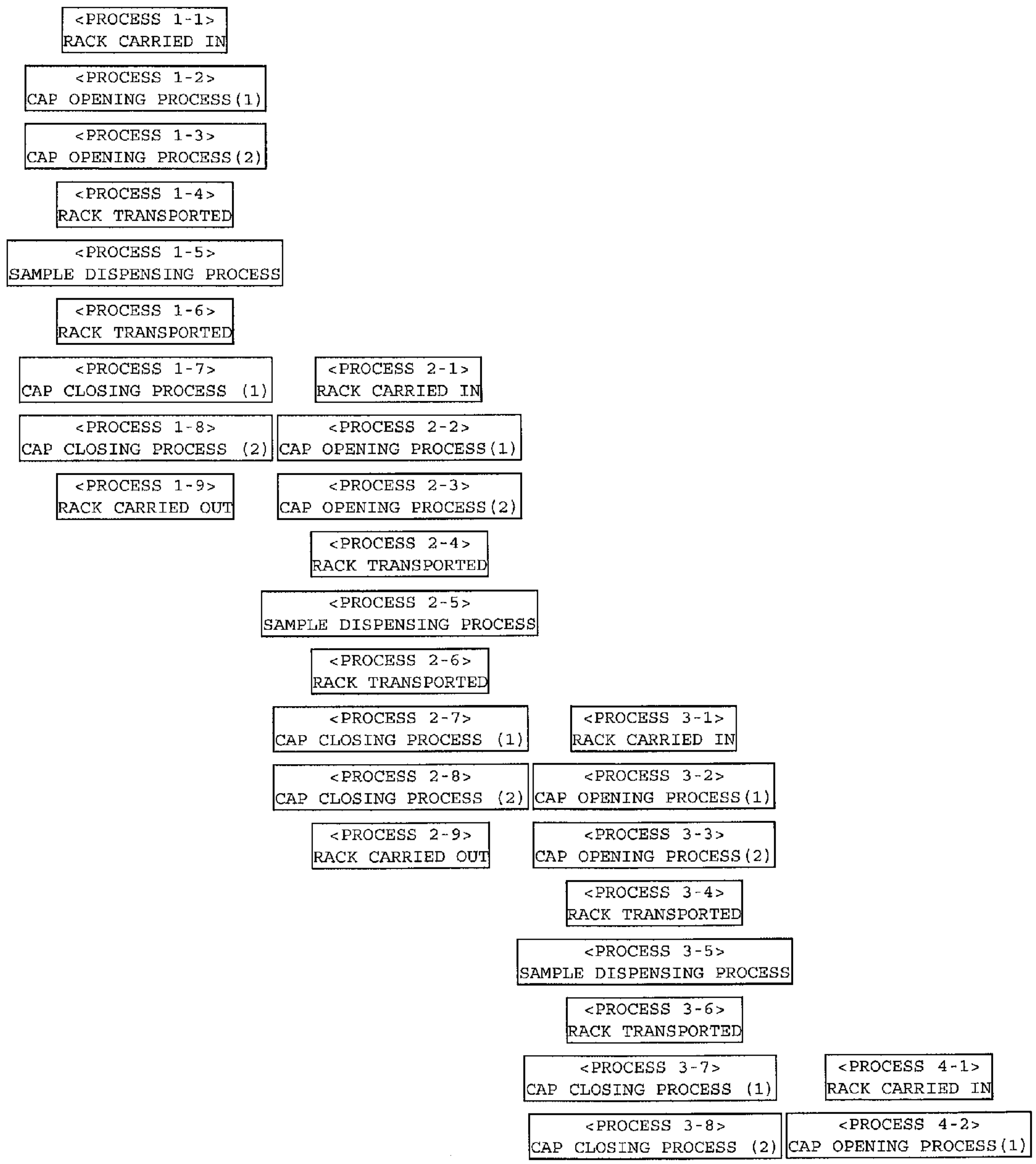
FIG. 6B is the flowchart showing the operations ranging from the process of transporting sample container to the process of opening their caps, the process of dispensing of the sample container, and the process of closing their caps according to the first and the second embodiments of the present invention.

FIG. 6 shows flowcharts of the operation patterns in two cases with emphasis on the first opening/closing unit 401, one of the two cases involving one transfer line A 45 (FIG. 6A), the other case involving two transfer lines (FIG. 6B). Where there are two transfer lines A 45 as shown in FIG. 6B, there are timings at which the cap opening process and the cap closing process may be carried out simultaneously (e.g., processes 1-7 through 1-9, and processes 2-1 through 2-3). This helps improve throughput of the unit.

Although this embodiment has been shown to have one opening/closing unit 401, this is not limitative of the present invention. Alternatively, if there are provided a plurality of opening/closing units, the efficiency in opening and closing the caps is boosted that much.

Third Embodiment

Figure 3F:
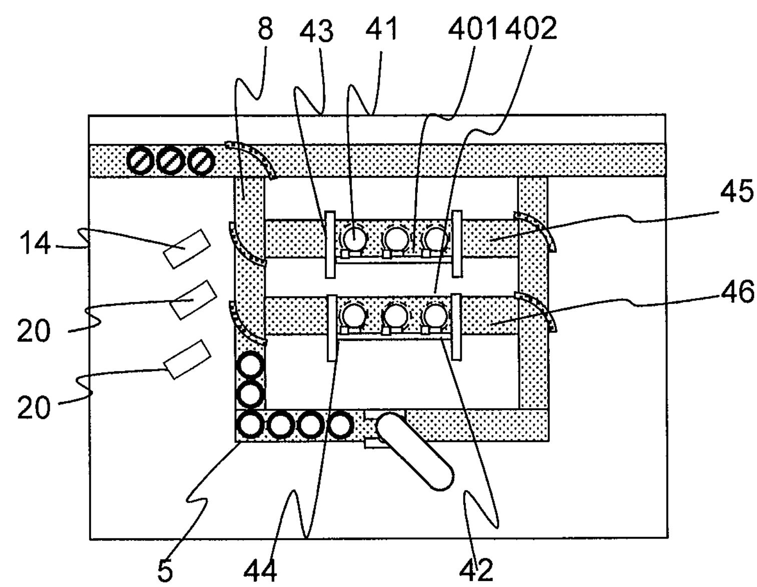
FIG. 3F is a schematic view showing a structure of an opening/closing unit according to a third embodiment of the present invention.
Figure 3G:
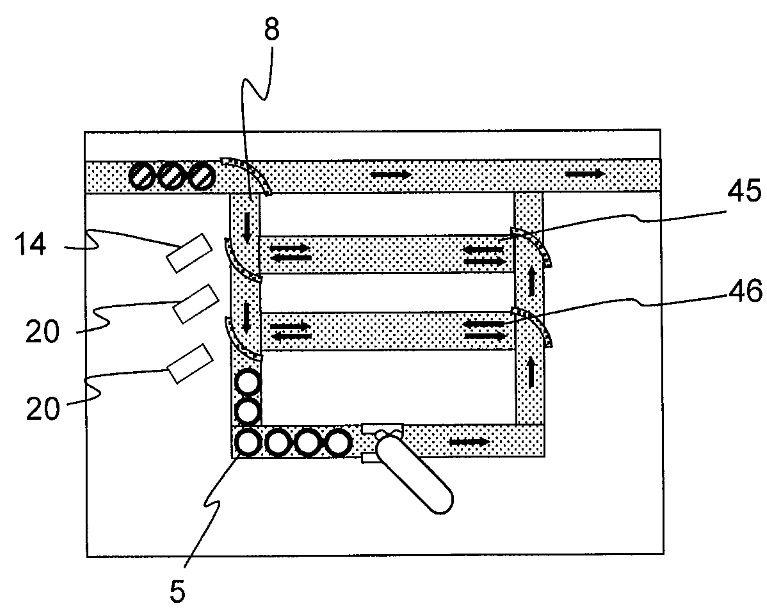
FIG. 3G is a schematic view showing a structure of a transport unit according to the third embodiment of the present invention.

FIGS. 3F and 3G are schematic plan views showing setups each including the first and the second opening/closing units 401 and 402 furnished respectively with transfer lines 45 and 46 as the third transfer line for the units.

The opening/closing position of the holder 5 transferred by the transport unit 8 is determined for cap status by the sample information identification unit 14. If the control computer determines that the cap opening process is needed, the control computer notifies the transport unit to that effect and, by referencing the sample information management unit 202, informs the transport unit of the opening/closing unit capable of carrying out the cap opening process on the rack in question.

The transport unit transports the holder along the first transport line. As the holder arrives at a branching point between the first transport line 83 and the third transport line 85 having the opening/closing unit 401 or 402 designated to perform the cap opening process, the ID reading unit 20 installed nearby reads the identification information on the sample containers or on the holder. The identification information thus read is transmitted to the sample information management unit 202 of the control computer and stored therein along with the information identifying the opening/closing unit that performs the cap opening process.

The cap opening/closing units (401, 402) are principally equipped with the chuck mechanisms (41, 42) that perform the cap opening and closing processes and retain the removed caps for management purposes, the transport arms (43, 44) that transport the chuck mechanisms, and the transfer lines 45 and 46 capable of transferring the holder 5 in reciprocating motion. The transport arms (43, 44) are principally furnished with drive mechanisms capable of moving the chuck mechanisms (41, 42) in three axial directions (Y, Y, and Z directions). The chuck mechanisms (41, 42) are capable of performing the processes of opening and closing the caps 7 and retaining the removed caps 7 until the cap closing process is carried out. Alternatively, the transport arms may be structured to move the chuck mechanisms in two axial directions so as to move test tubes in these directions accordingly.

FIG. 3F is a schematic view in which the chuck mechanisms (41, 42) of the cap opening/closing units (401, 402) and the transport arms (43, 44) are not shown. The transfer line 45 is provided as a transfer line subject to the opening and closing processes by the first opening/closing unit 401, and the transfer line 46 is furnished as a transfer line subject to the opening and closing processes by the second opening/closing unit 402.

The opening/closing units (401, 402) of this embodiment are capable of simultaneously opening and closing the sample containers 6 mounted on a plurality of holder 5.

Fourth Embodiment

Figure 3H:
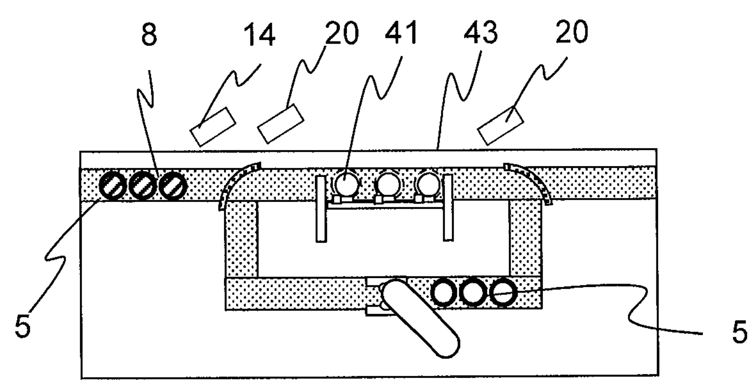
FIG. 3H is a schematic view showing a structure of an opening/closing unit according to a fourth embodiment of the present invention.
Figure 3I:
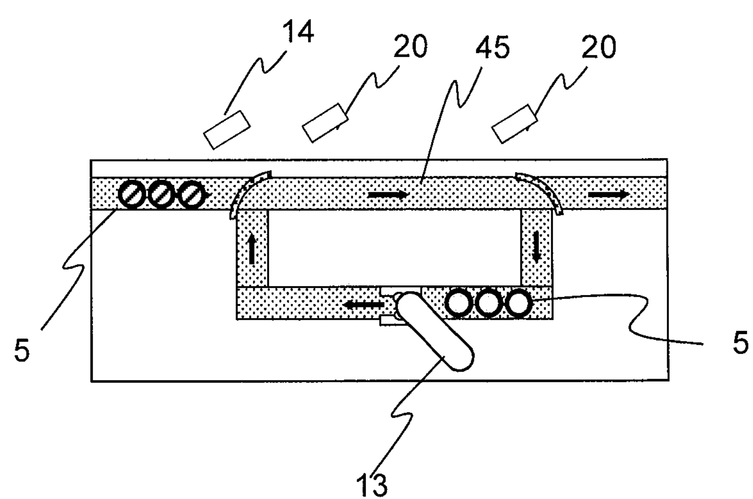
FIG. 3I is a schematic view showing a structure of a transport unit according to the fourth embodiment of the present invention.

FIGS. 3H and 3I are schematic plan views showing setups each including the opening/closing unit 4, and the transport line 45 acting as a transport line for the transport unit 8 and opening/closing unit.

The opening/closing position of the holder 5 transferred by the transport unit 8 is determined for cap status by the sample information identification unit 14. If the control computer determines that the cap opening process is needed, the control computer notifies the transport unit to that effect and, by referencing the sample information management unit 202, informs the transport unit of the opening/closing unit capable of carrying out the cap opening process on the rack in question.

The transport unit transports the holder along the first transport line. As the holder arrives at a branching point between the first transport line 8 and the third transport line 85 having the opening/closing unit 401 designated to perform the cap opening process, the ID reading unit 20 installed nearby reads the identification information on the sample containers or on the holder. The identification information thus read is transmitted to the sample information management unit 202 of the control computer and stored therein along with the information identifying the opening/closing unit that performs the cap opening process.

The cap opening/closing unit (401) is principally equipped with the chuck mechanism (41) that performs the cap opening and closing processes and retains the removed caps for management purposes, the transport arm (43) that transports the chuck mechanism, and the transfer line 45 capable of transferring the holder 5 in reciprocating motion.

The transport arm (43) is principally furnished with drive mechanisms capable of moving the chuck mechanism (41) in three axial directions (X, Y, and Z directions). The chuck mechanism (41) is capable of performing the processes of opening and closing the caps 7 and retaining the removed caps 7 until the cap closing process is carried out. Alternatively, the transport arm may be structured to move the chuck mechanism in two axial directions so as to move test tubes in these directions accordingly.

FIG. 3I is a schematic view in which the chuck mechanism (41) of the cap opening/closing unit (401) and the transport arm (43) are not shown. The transfer line 45 composed of a transfer line 451 is provided as the transfer line subject to the opening and closing processes by the first opening/closing unit 401.

The opening/closing unit (401) of this embodiment is capable of simultaneously opening and closing the sample containers 6 mounted on a plurality of holders 5.

The effects of this embodiment structured as described above are explained below.

Figure 9:
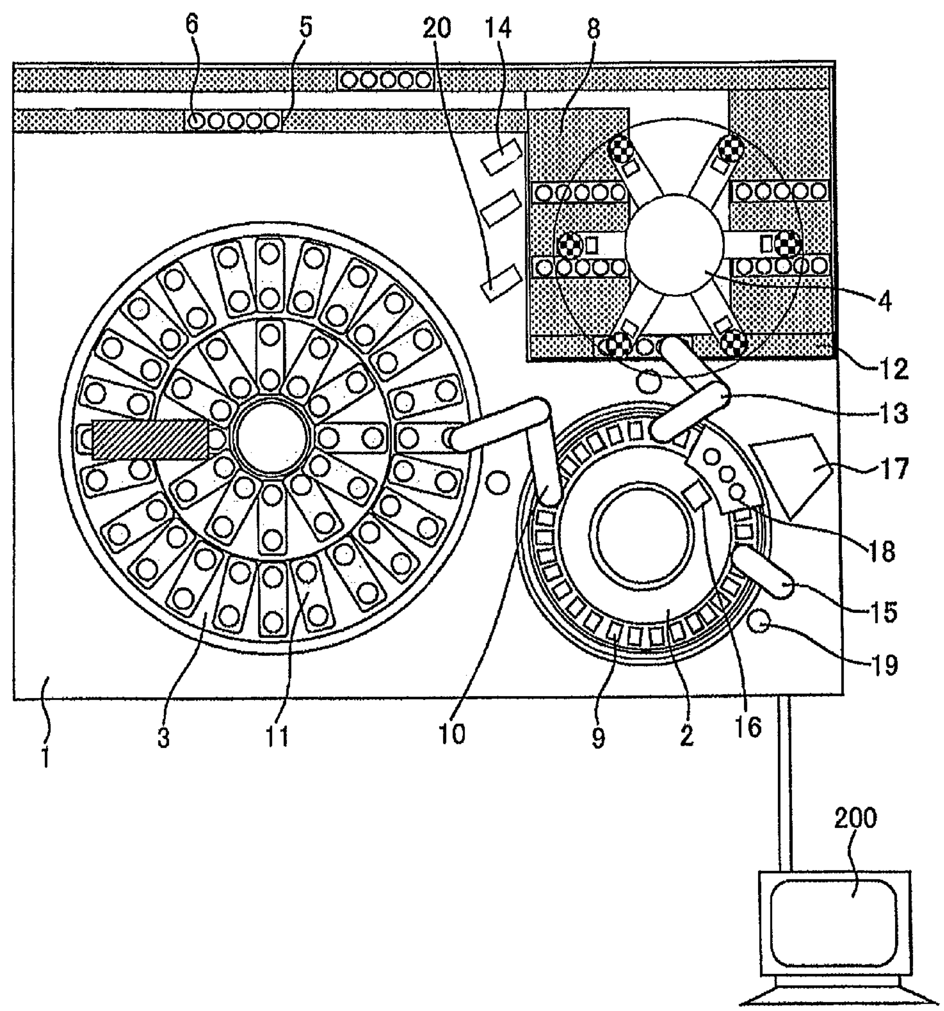
FIG. 9 is a schematic view showing an overall configuration of an automatic analysis system furnished with a prior-art opening/closing device for opening and closing sample container.

According to the prior art, during the dispensing process of the automatic analysis system regarding containers that need to have their caps opened and closed, it was customary to open and close the caps one after another as the containers are being transferred. Where the cap opening and closing processes are performed in the same position, the cap opening/closing mechanism keeps holding each cap from the time it is opened until it is again closed on the corresponding container. During that time, no other container can undergo the cap opening and closing processes, which can amount to a considerable loss of time. As a prior-art example, FIG. 9 shows an automatic analysis system, as a cap opening/closing unit 4, furnished with a cap opening/closing device with mechanisms for rotating a plurality of opening/closing units. In this case, the cap opening process, sample dispensing process, and cap closing process following dispensing are all carried out on the sample line 12. Generally, it takes longer to perform the cap opening and closing processes than the dispensing process. If it takes, say, 10 seconds to go through one cycle ranging from opening to closing of each cap, then the number of processed caps per hour amounts to 3600/10=360 (processed caps/hour) at most.

Even if a plurality of cap opening/closing units and a plurality of dispensing units are provided for the purpose of boosting throughput, where these units are installed in series, there is the problem of racks getting stranded on the sample line 12. Where these units are installed in parallel, there occurs the problem of space efficiency around the units deteriorated in terms of access to other mechanisms. If any of the cap opening process, dispensing process and cap closing process is unsuccessful, then the throughput of the entire automatic analysis system could be lowered.

Meanwhile, where the cap opening process and the cap closing process are carried out in different positions, it is necessary selectively to transport the removed cap fit for each sample container yet to be closed up to the cap closing position where the cap closing process is to be performed. It follows that there has to be separate means for transporting the caps. In such a system, the time required to go through one cycle ranging from opening to closing of each cap can be dependent on the time it takes to perform the cap opening or closing process. For example, if the cap opening process takes 6 seconds per container and the cap closing process 3 seconds per container, then the processing speed of the sample sampling process takes 6 seconds per container. That is, the time required to go through one cycle ranging from opening to closing of each cap is 15 seconds per container, which amounts to processing 600 containers per hour.

Under these circumstances, the system equipped with such opening/closing mechanisms has been challenged with the problem of how to achieve higher throughput.

According to the embodiments of this invention, the dedicated transfer lines (transfer lines A 45, 451, 452) are provided to transport samples to the opening/closing unit 401 so that the caps 7 removed from the sample containers 6 may be attached again to the original sample containers 6. Because the opening/closing unit itself does not move out of the range of these transport lines, there is no need for sophisticated mechanisms to move the opening/closing unit over extended distances.

There is also provided a management system that manages sample information and cap information. Based on the information from the management system, an optimal route for transporting sample containers is selected so that the removed caps may be attached to the same sample containers as before the cap opening process. This ensures that the removed caps are again attached to the optimally fit sample containers.

Furthermore, the opening/closing unit has a plurality of opening/closing means functioning at one time so that a plurality of sample containers may be opened or closed simultaneously. This promises a higher processing speed than with prior-art setups.

This invention is implemented by setting up a branching point upstream and downstream of the sample line leading to the transport line for the opening/closing unit. The racks that need to undergo the cap opening and closing processes are transported via the branching point to the dedicated transfer line that deals with these processes to be performed on each rack. The racks on which the cap opening and closing processes have ended are each returned to the initial line. According to this method, the position where the caps of the sample containers are opened and closed is established separately from the position where the samples are dispensed. This ensures that the cap opening and closing processes do not affect the sample dispensing process. That in turn makes it possible to provide sample container opening/closing means and sample dispensing means in keeping with the throughput of the automatic analysis system.

According to the present invention, the automatic analysis system includes an analysis system that measures the physical properties of samples (e.g., biological samples such as serum and urine, or liquid mixtures of samples with reagents), a pretreatment system that processes samples before the measurement of their physical properties, and a system that integrates the pretreatment system with the analysis system. The automatic analysis system is equipped with processing units that perform such diverse processes as the container cap opening process, dispensing process, container cap closing process, stirring process, and analyzing process; and a transport unit that transports samples between the processing units. Although an automatic analysis unit may be included in the system, the system need only be furnished as a minimum with the cap opening unit, cap closing unit, and dispensing unit along with the transport unit that transports samples between these units.

The cap may be formed of rubber, plastic or the like. Acting to keep the sample from seeping out of the sample container, the cap may be of a screw type or a friction type.

The sample container is a container that encloses the sample targeted for measurement. The sample containers may be mounted on the rack or on the holder as long as they can be transferred.

The cap opening/closing unit may be any unit as long as it is managed to retain a plurality of removed caps and to close the opened containers with the removed caps thus retained. Conceivably, the cap opening/closing unit may use a robot arm to retain and manage the caps, utilize a turntable to rotatively retain and manage the caps, or employ an elevator to vertically retain and manage the caps. The caps may be retained and managed in any suitable manner as long as they, along with the sample containers, are prevented from getting contaminated. Contamination prevention is generally accomplished by means of shielding, by performing suction and disposal processes, or by carrying out cleaning and sterilizing processes.

The transport unit for transporting sample containers may be of any type as long as it is capable of transferring the rack or holder mentioned above. Generally, the transport unit may be of a conveyor belt type, a ratchet feed type, or a robot arm type.

DESCRIPTION OF REFERENCE CHARACTERS

1 Housing
2 Reaction disk
3 Reagent disk
4 Opening/closing unit
5 Rack
6 Sample container
7 Cap
8 Transport unit
9 Reaction vessel
10 Reagent probe
11 Reagent container
12 Sample line
13 Sample probe
14 Sample information identification unit
15 Stirring unit
16 Light source
17 Optical detector
18 Container cleaning mechanism
19 Cleaning port
20 ID reading unit
21 Sample information management mechanism
41, 42 Chuck mechanism
43, 44 Transport arm
45 Transfer line A
46 Transfer line B
121 Sample collection position
200 Control computer
202 Sample information management unit
401, 402 Opening/closing unit
451, 452 Transfer line

The invention claimed is:

1. An automatic analysis system equipped with a transport unit which retains and transports sample containers having removable caps, the automatic analysis system comprising:

a sample probe which pipets samples contained in the sample containers; and a plurality of cap opening/closing units, each of which opens and closes the caps of the sample containers, wherein the transport unit includes:

a first transport line which transports the sample containers, which have had their caps removed, to a sample line adjacent to the sample probe;

a second transport line which transports the sample containers from the sample line, having undergone pipetting of the samples by the sample probe, away from the sample probe; and a third transport line which connects to the first transport line and the second transport line, transports the sample containers to and from the cap opening/closing units which are adjacent to the third transport line, wherein each of the plurality of cap opening/closing units retains the caps opened by performing a cap opening process on given samples and closes the retained caps by carrying out a cap closing process on the same samples, wherein the third transport line has a plurality of transport lines arranged in parallel to transport the samples to a position where the caps thereof may be opened and closed by the plurality of cap opening/closing units.

2. The automatic analysis system according to claim 1, further comprising a control unit which controls each of the cap opening/closing units in such a manner as to perform:

a cap opening process on the caps of the sample containers transported from the first transport line to the third transport line; and a cap closing process on the caps of the sample containers transported from the second transport line to the third transport line.

3. The automatic analysis system according to claim 1, further comprising:

a storage medium which stores sample information identifying the samples;

a plurality of ID reading units which read the sample information of the samples before the cap opening/closing units perform the cap opening process and which read the sample information when the samples are transported from the second transport line to the third transport line, and wherein the control unit determines the cap opening/closing unit which should perform the cap closing process based on the result of the reading by at least one of the plurality of ID reading units.

4. The automatic analysis system according to claim 1, wherein each of the cap opening/closing units include chuck mechanisms;

wherein each of the cap opening/closing units has the plurality of chuck mechanisms arranged as a block in a plurality of rows; and wherein each of the chuck mechanisms arranged in the block, respectively, perform the opening and closing processes on a plurality of caps simultaneously.

5. The automatic analysis system according to claim 4, wherein the third transport line has the plurality of transport lines arrayed corresponding to the cap opening/closing means arranged in a plurality of rows.

6. The automatic analysis system according to claim 1, wherein a type of the cap attached to a given sample container is identified;

wherein cap opening/closing methods classified by the cap type are stored in a storage medium;

wherein a determination is made as to whether or not the cap opening/closing process may be performed based on the type of cap identified; and wherein, given a sample container for which the cap opening/closing process may be performed according to the determination, a control unit causes the cap opening/closing method corresponding to the sample container in question to be retrieved from the storage medium and implemented to execute the cap opening/closing process, and wherein, given a sample container for which the cap opening/closing process may not be performed according to the determination, the control unit causes the cap opening/closing method corresponding to the sample container in question to be retrieved from the storage unit and implemented to execute the cap opening process, causes a cap that is appropriate to close the sample container to be supplied, and/or causes the cap closing process to be performed to close the sample container with the appropriate cap.

7. The automatic analysis system according to claim 6, wherein the sample containers are allowed to wait on the second transport line, and wherein the control unit instructs to change the order in which the sample containers are transported, based, at least in part, on the identified cap type of the caps attached to the sample containers.

8. The automatic analysis system according to claim 1, wherein a cap opened/closed state of the sample containers is detected, and wherein, based on the detected opened/closed state of the sample containers, when the opening or closing of a particular cap has failed, the opening or closing of that particular cap is repeated.

9. The automatic analysis system according to claim 1, wherein the third transport line allows the sample containers to move thereon in reciprocating motion.

* * * * *